(12) United States Patent
Heneghan et al.

(10) Patent No.: US 12,070,325 B2
(45) Date of Patent: Aug. 27, 2024

(54) FATIGUE MONITORING AND MANAGEMENT SYSTEM

(71) Applicant: RESMED SENSOR TECHNOLOGIES LIMITED, Clonskeagh (IE)

(72) Inventors: Conor Heneghan, San Diego, CA (US); Ciaran Gerard McCourt, Parkland, FL (US); Stephen McMahon, Dundrum (IE); Redmond Shouldice, Clonskeagh (IE)

(73) Assignee: ResMed Sensor Technologies Limited (IE)

( * ) Notice: Subject to any disclaimer, the term of this patent is extended or adjusted under 35 U.S.C. 154(b) by 160 days.

(21) Appl. No.: 17/523,599

(22) Filed: Nov. 10, 2021

(65) Prior Publication Data

US 2022/0061752 A1    Mar. 3, 2022

Related U.S. Application Data

(63) Continuation of application No. 15/028,311, filed as application No. PCT/US2014/059311 on Oct. 6, 2014, now Pat. No. 11,197,633.

(30) Foreign Application Priority Data

Oct. 9, 2013  (AU) ............................... 2013903881
Jun. 19, 2014 (AU) ............................... 2014902350

(51) Int. Cl.
*A61B 5/00*    (2006.01)
*A61B 5/0533*  (2021.01)
(Continued)

(52) U.S. Cl.
CPC .......... *A61B 5/4815* (2013.01); *A61B 5/0022* (2013.01); *A61B 5/0533* (2013.01);
(Continued)

(58) Field of Classification Search
CPC ................... G16H 50/20; G16H 50/30; A61B 2560/0242; A61B 5/0022; A61B 5/02055;
(Continued)

(56) References Cited

U.S. PATENT DOCUMENTS

| 4,944,310 A | 7/1990 | Sullivan |
|---|---|---|
| 6,532,959 B1 | 3/2003 | Berthon-Jones |

(Continued)

FOREIGN PATENT DOCUMENTS

| CA | 2578855 A1 | 8/2008 |
|---|---|---|
| EP | 2278508 A1 | 1/2011 |

(Continued)

OTHER PUBLICATIONS

CA Office Action Search Report Application No. 2,925,548 dated Feb. 20, 2020.
(Continued)

*Primary Examiner* — Scott Luan
(74) *Attorney, Agent, or Firm* — Botos Churchill IP Law LLP

(57) ABSTRACT

A system monitors fatigue of a user. The system (100) may include one or more data sources, such as a non-obtrusive sleep sensor, configured to generate objective sleep measures of the user. The system may also include a fatigue monitoring module, which may be configured to generate an assessment, such as in one or more processors, of the fatigue state of the user based on the data from the one or more data sources.

28 Claims, 7 Drawing Sheets

(51) Int. Cl.
  *A61B 5/11*     (2006.01)
  *A61B 7/00*     (2006.01)
  *A61M 16/00*    (2006.01)
  *G16H 50/20*    (2018.01)
  *G16H 50/30*    (2018.01)
  *A61B 5/0205*   (2006.01)
  *A61B 5/024*    (2006.01)
  *A61B 5/0245*   (2006.01)
  *A61B 5/08*     (2006.01)
  *A61B 5/18*     (2006.01)
  *A61B 5/291*    (2021.01)
  *A61B 5/352*    (2021.01)
  *A61B 5/369*    (2021.01)

(52) U.S. Cl.
  CPC ............ *A61B 5/1118* (2013.01); *A61B 7/003* (2013.01); *A61M 16/0069* (2014.02); *G16H 50/20* (2018.01); *G16H 50/30* (2018.01); *A61B 5/02055* (2013.01); *A61B 5/02405* (2013.01); *A61B 5/0245* (2013.01); *A61B 5/0816* (2013.01); *A61B 5/18* (2013.01); *A61B 5/291* (2021.01); *A61B 5/352* (2021.01); *A61B 5/369* (2021.01); *A61B 5/4818* (2013.01); *A61B 5/7253* (2013.01); *A61B 5/7257* (2013.01); *A61B 5/7264* (2013.01); *A61B 5/746* (2013.01); *A61B 2560/0242* (2013.01)

(58) Field of Classification Search
  CPC . A61B 5/02405; A61B 5/0245; A61B 5/0533; A61B 5/0816; A61B 5/1118; A61B 5/18; A61B 5/291; A61B 5/352; A61B 5/369; A61B 5/4815; A61B 5/4818; A61B 5/7253; A61B 5/7257; A61B 5/7264; A61B 5/746; A61B 7/003; A61M 16/0069
  See application file for complete search history.

(56) References Cited

U.S. PATENT DOCUMENTS

| | | | |
|---|---|---|---|
| 8,075,484 B2 | 12/2011 | Moore-Ede | |
| 2005/0065560 A1 | 3/2005 | Lee et al. | |
| 2005/0115561 A1* | 6/2005 | Stahmann | A61B 5/02055 128/204.23 |
| 2005/0217674 A1 | 10/2005 | Burton | |
| 2008/0033304 A1 | 2/2008 | Dalal et al. | |
| 2009/0118631 A1 | 5/2009 | Gavish et al. | |
| 2010/0049008 A1 | 2/2010 | Doherty | |
| 2010/0099954 A1 | 4/2010 | Dickinson et al. | |
| 2010/0292545 A1 | 11/2010 | Berka et al. | |
| 2011/0015495 A1 | 1/2011 | Dothie et al. | |
| 2011/0154958 A1 | 1/2011 | Dothie et al. | |
| 2011/0124979 A1 | 5/2011 | Heneghan et al. | |
| 2011/0178377 A1 | 7/2011 | Heneghan et al. | |
| 2011/0245633 A1 | 10/2011 | Goldberg et al. | |
| 2011/0251985 A1* | 10/2011 | Waxman | G16H 10/60 706/20 |
| 2012/0214143 A1 | 8/2012 | Severson et al. | |
| 2012/0316845 A1 | 12/2012 | Grey et al. | |
| 2012/0329020 A1 | 12/2012 | Mollicone et al. | |
| 2013/0006064 A1 | 1/2013 | Reiner | |
| 2013/0131464 A1 | 5/2013 | Westbrook et al. | |
| 2013/0314243 A1 | 11/2013 | Le | |
| 2016/0270718 A1 | 9/2016 | Heneghan et al. | |

FOREIGN PATENT DOCUMENTS

| | | |
|---|---|---|
| EP | 3054836 A1 | 8/2016 |
| EP | 3054836 A4 | 6/2017 |
| JP | H0341927 A | 2/1991 |
| JP | H08256995 A | 10/1996 |
| JP | 2005074012 A | 3/2005 |
| JP | 2005261669 A | 9/2005 |
| JP | 2005304941 A | 11/2005 |
| JP | 2006061270 A | 3/2006 |
| JP | 2007222276 A | 9/2007 |
| JP | 2007531592 | 11/2007 |
| JP | 2008000222 A | 1/2008 |
| JP | 2010099173 A | 5/2010 |
| JP | 201136649 A | 2/2011 |
| JP | 2013022360 A | 2/2013 |
| JP | 2013128659 A | 7/2013 |
| WO | 0044580 A1 | 8/2000 |
| WO | 2005039415 A1 | 5/2005 |
| WO | 2006000166 A1 | 1/2006 |
| WO | 2006006634 A1 | 1/2006 |
| WO | 2007138930 A1 | 12/2007 |
| WO | 2009115073 A3 | 12/2009 |
| WO | 2010042615 A3 | 7/2010 |
| WO | 2010091168 A1 | 8/2010 |
| WO | 2013009988 A1 | 1/2013 |

OTHER PUBLICATIONS

Canadian Office Action issued in corresponding Canadian application No. 2925548 on Apr. 10, 2018.
Extended European Search Report for Application No. 14852804.5 dated May 23, 2017.
International Search Report and Written Opinion for Application No. PCT/US2014!059311 dated Jan. 12, 2015.
Japanese Office Action issued in corresponding JP application No. 2016-521736 on Jul. 18, 2018.
JP Office Action issued Mar. 2, 2021 for JP Patent Application No. 2020-085229.
NSF (National Sleep Foundation), 2013. http://www.sleepfoundation.org/article/sleep related problems/excessive sleepiness and-sleep.
State of Queensland, Department of Natural Resources and Mines, 2013. Guidance Note for Fatigue Risk Management.
Åhsberg, E , Dimensions of fatigue in different working populations. Scandinavian Journal of Psychology, 41: 231-241. 2000 http://onlinelibrary.wiley.com/doi/10.1111/1467 9450.00192/pdf.
Barker , et al., Fatigue, performance and the work environment: a survey of registered nurses, Journal of Advanced Nursing, (2010).
Belenky, G , et al., Patterns of performance degradation and restoration during sleep restriction and subsequent recovery: a sleep dose-response study. J Sleep Res, vol. 12 No. 1. http://onlinelibrary.wiley.com/doi/10.1046/j.1365 2869.2003.00337.x/pdf 2003.
Berglund, Shahly , et al., The Associations of Insomnia With Costly Workplace Accidents and Errors: Results From the America Insomnia Survey. Arch Gen Psychiatry. 2012: 69(10):1054-10.
Colten , et al., Institute of Medicine (US) Committee on Sleep Medicine and Research; Sleep Disorders and Sleep Deprivation: An Unmet Public Health Problem. Washington (DC): National Academies Press (US); 2006.
Dawson , et al., Fatigue, alcohol and performance impairment. Nature, 388: 235. 1997.
Dinges , et al., Cumulative sleepiness, mood disturbance, and psychomotor vigilance performance decrements during a week of sleep restricted to 4-5 hours per night. Sleep 1997; 20 (4):267-77.
Harrington, J , Shiftwork and Health: A Critical Review of the Literature. Report to the Medical Advisory Service, UK Health and Safety Executive. 1978.
Jackowska , et al., Sleep problems and heart rate variability over the working day, Journal of Sleep Research, vol. 21, Issue 4, Feb. 2012.
Nicholson, PJ , et al., Shift work, health, the working time regulations and health assessments. Occup Med (Lond). Apr. 1999;49(3):127-37. http://occmed.oxfordjournals.org/content/49/3/127.full.pdf 1999.
Sasaki, T. , Overtime, job stressors, sleep/rest, and fatigue of Japanese workers in a company. https://www.jstage.jst.go.jp/article/indhealth/45/2/45_2_237/_pdf 2007.
Shambroom, Fabregas , Age Related Changes in Objectively Measured Sleep Observed in a Large Population in the Home, available through myzeo.com.
Trejo , et al., EEG-Based Estimation of Mental Fatigue. http://aiolos.um.savba.sk/~roman/Papers/hci07_1.pdf.

(56) References Cited

OTHER PUBLICATIONS

Zichermann, G , et al., Introduction to Gamification by Design: Implementing Game Mechanics in Web and Mobile Apps (1st ed.). Sebastopol, California: O'Reilly Media. (Aug. 2011).
Office Action issued in corresponding Japanese Patent Application No. 2021-205063, mailed Nov. 29, 2022, 6 pages.

* cited by examiner

FATIGUE MONITORING AND MANAGEMENT SYSTEM

1 CROSS-REFERENCE TO RELATED APPLICATIONS

This application is a continuation of U.S. patent application Ser. No. 15/028,311, filed on Apr. 8, 2016, which is national phase entry under 35 U.S.C. § 371 of International Application No. PCT/US14/059311, filed Oct. 6, 2014, published in English, which claims priority from Australian Provisional Patent Application Nos. 2014902350, filed Jun. 19, 2014 and 2013903881, filed Oct. 9, 2013, all of which are incorporated herein by reference

STATEMENT REGARDING FEDERALLY SPONSORED RESEARCH OR DEVELOPMENT

Not Applicable

2 THE NAMES OF PARTIES TO A JOINT RESEARCH DEVELOPMENT

Not Applicable

3 SEQUENCE LISTING

Not Applicable

4 BACKGROUND OF THE INVENTION

4.1 FIELD OF THE INVENTION

The present technology relates to monitoring and management of fatigue. In particular, the present technology relates to systems and methods for use in monitoring and management of fatigue.

4.2 DESCRIPTION OF THE RELATED ART

The respiratory system of the body facilitates gas exchange.

The nose and mouth form the entrance to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone.

4.2.1 Respiratory Disorders

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

4.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

The application of a supply of air at positive pressure to the entrance of the airways of a patient is facilitated by the use of a patient interface, such as a nasal mask, a full-face mask, or nasal pillows.

The air at positive pressure may be supplied to the airway of a patient by a respiratory pressure therapy (RPT) device such as a motor-driven blower. The outlet of the RPT device is connected via a flexible delivery conduit to a patient interface as described above.

4.2.3 Fatigue

A guidance note on fatigue issued by the Australian state of Queensland (2013) defines fatigue as a state of impairment that can include physical and/or mental elements, associated with lower alertness and reduced performance. There are a number of contributing factors to fatigue, typically related to:

Poor sleep quality (e.g., due to family/recreational factors, stress, noise, respiratory disorders and other health issues). Poor sleep quality is a significant issue globally and impacts up to 60% of the adult population.

Extended wakefulness, defined as the time in hours since the last sleep.

One of the primary causes of fatigue among Americans is self-imposed wakefulness or sleep deprivation. In other words, poor "sleep hygiene" whereby a person deliberately restricts their sleep and/or goes to bed at different times during the week and weekend, leading to Sunday night insomnia. For example, a person may skip sleep in an attempt to get more done, and remain engaged with a laptop, tablet or smartphone 'around the clock' (NSF, 2013).

More generally, fatigue can be considered to be a complex problem, with multiple factors involved. Fatigue due to loss of sleep quality or quantity can be experienced after a short period of exposure to sleep loss (known as acute fatigue) or over a longer period of time where sleep loss has accumulated due to sleep disruption or lack of restorative sleep (referred to as cumulative fatigue). Mental (cognitive) fatigue can for example manifest as: impaired alertness, coordination, and decision making; emotional impact; and micro-sleeps during tasks. Restorative (deep, slow wave) sleep is associated with physical recharge, i.e. reducing physical fatigue. Cognitive (REM) sleep is associated with mental recharge.

It has been estimated that sleep-related fatigue costs businesses $150 billion a year in absenteeism and workplace accidents. It has been noted that error rates increase exponentially with linear increases in psychometric measures of fatigue (Dinges, et al., 1997). Insomnia has been linked to 7% of all costly workplace accidents and errors and 24% of workplace mishaps overall (Shahly et al., 2012). Dawson and Reid (1997) equate the performance impairment caused by fatigue with that due to alcohol intoxication, and show that moderate levels of fatigue produce higher levels of impairment than the proscribed level of alcohol intoxication. Poor-quality sleep and inadequate recovery lead to increased fatigue, decreased alertness, and impaired performance in a variety of cognitive psychomotor tests (Harrington, 1978; Nicholson & D'Auria, 1999). Barker & Nussbaum's (2010) study of registered nurses reported that mental fatigue levels were higher than physical fatigue levels, and that acute fatigue levels were higher than chronic fatigue levels. All fatigue dimensions and states were negatively correlated with perceived performance. The Swedish Occupational Fatigue Inventory (SOFI) assessed perceived fatigue related to work across four dimensions: lack of energy, physical exertion, physical discomfort and lack of motivation. The lack of energy dimension was used to measure total fatigue, the lack of motivation dimension to measure mental fatigue, and the physical exertion and physical discomfort dimensions as measures of physical fatigue (Åhsberg, 2000).

4.2.4 Previous Approaches

Previous approaches to fatigue management rely primarily on review of rostered hours/shifts and perhaps subject-reported episodes of sleep.

U.S. Pat. No. 8,075,484 B2 outlines "a system and method for assessing and modifying fatigue, an input device receives current work-rest pattern and/or sleep data from an individual. A data aggregation and processing platform combines the current work-rest pattern and/or sleep data with previous data related to the individual to generate a fatigue assessment result, a diagnostic assessment result, and a corrective intervention result. At least one output display outputs the fatigue assessment result, diagnostic assessment result and corrective intervention result in a user-readable format to a user. The user uses this information to revise the work-rest pattern to reduce or control future fatigue risk".

EP publication no. 2278508 A1 outlines: "A sleep management method and system for improving the quality of sleep of a user which monitors one or more objective parameters relevant to sleep quality of the user when in bed and receives from the user in waking hours via a portable device such as a mobile phone feedback from objective test data on cognitive and/or psychomotor performance.".

US application no. 20120316845 A1 outlines: "Distributed computing methods and systems are disclosed, wherein intensive fatigue-risk calculations are partitioned according to available computing resources, parameters of the fatigue-risk calculation, time-sensitive user demands, and the like. Methods are disclosed wherein execution-cost functions are used to allocate accessible computing resources. Additional methods include partitioning calculation tasks by user-prioritized needs and by general mathematical features of the calculations themselves. Included herein are methods to calculate only prediction-maximum likelihoods instead of full probability distributions, to calculate prediction likelihoods using Bayesian prediction techniques (instead of full re-tabulation of all data), to collate interim results of fatigue-risk calculations where serial results can be appropriately collated (e.g., serial time-slice independence of the cumulative task involved), to use simplified (e.g., linear, first-order) approximations of richer models of fatigue prediction, to assign user-identified priorities to each computational task within a plurality of such requests, and the like."

US application no. 20120329020 A1 outlines: "A method is provided for ascertaining personalized education information related to one or more fatigue-related individual traits of a subject. The method involves: receiving first input data indicative of an expression of one or more fatigue-related individual traits of the subject; estimating trait values for the one or more fatigue-related individual traits, wherein estimating the trait values comprises: using the first input data and a fatigue model, which relates a fatigue level of the subject to a set of model parameters, to estimate values for the set of model parameters; and evaluating one or more trait-estimation functions using the estimated values for the set of model parameters; and determining personalized education information about the one or more fatigue-related individual traits of the subject based on the estimated trait values."

PCT Publication no. WO 2006000166 A1 outlines operator fatigue detection from operator muscular activity, and assessment using fatigue assessment rules obtained using a data mining method from an operator for whom the extent of fatigue is already known.

PCT Publication no. WO 2000044580 A1 outlines: "Apparatus for determining a vigilance state of a subject such as a driver of a vehicle or the like. The apparatus includes means (1 to 11) for monitoring one or more physiological variables such as EEG, EMG and EOG signals associated with the subject. The apparatus also includes means (13 to 16) for deriving from the one or more variables data representing physiological states of the subject corresponding to the or each variable and means (17) for determining from the data when the vigilance state of the subject is below a predetermined threshold. The apparatus may include means for intervening with the control of the vehicle in the event that the vigilance state of the driver is below the predetermined threshold."

CA Application no. 2578855 A1 outlines a system that includes an employee module for providing skills and tools to employees to self-assess, regulate and manage personal levels of sleep, stress and fatigue and a corporate module for providing guidelines for acceptable levels of performance and for assisting employees in meeting the guidelines through management of personal sleep, stress and fatigue levels. An actigraph-based personal monitoring device is used to record individual employee levels of fatigue at work and quantity of sleep received while off work for comparison against company guidelines.

PCT Publication no. WO 2010042615 A3 outlines: "Systems and methods for optimizing the sleep and post-sleep performance of individuals regardless of their environment and time available for sleep are provided. The systems and methods take into account factors that determine the effects of a sleep episode on dexterity, cognitive functions and the subjective feeling of fatigue after sleeping: duration and sleep architecture of the sleep episode, point on the circadian cycle at which the episode occurred, the amount of sleep debt accumulated prior to the episode and the subject's susceptibility to sleep deprivation. The systems and methods include monitoring of sleep architecture over a longer period of time, measurement of accumulated sleep debt and assessment and/or tailoring of the sleep architecture for each subsequent sleep episode, determining a desired sleep state in which the subject should be in, and generating sensory stimuli for guiding the subject to the desired sleep state."

PCT Publication no. WO 2009115073 A3 outlines a method and an apparatus for maintaining, restoring or increasing the attention and alertness of a fatigued person and for preventing accidents, damage, or incorrect decisions as a result of excess fatigue, particularly during extended monotonous activities.

PCT Publication no. WO 2005039415 A1 outlines: "It is possible to quantify a fatigue degree and display it. A fatigue degree measuring device (1) includes: biological signal peak value detection means (23) for detecting a peak value of each cycle of the raw waveform of biological signal data; power value calculation means (24) for calculating a difference between the peak value of the upper limit side and a peak value of the lower limit side for predetermined time range from the peak values obtained from the biological signal peak value detection means (23) and setting the difference as a power value; and power value inclination calculation means (25) for calculating the inclination of the power value. The time-series signal of the power value inclination is subjected to an absolute value processing and an integrated value is calculated. The integrated value is obtained as a fatigue degree. Thus, it is possible to quantify the human fatigue degree."

PCT Publication no. WO 2007138930 A1 outlines: "A fatigue estimation device has a body motion detection section (2) for continuously detecting the frequency of a user's activity as the level of activity. The level of activity detected by the body motion detection section (2) is outputted to a fatigue detection section (3) for estimating the level of user's fatigue based on the level of activity."

US Application no. 20110178377 A1 outlines: "An apparatus, system, and method for the measurement, aggregation and analysis of data collected using non-contact or minimally-contacting sensors provides quality of life parameters for individual subjects, particularly in the context of a controlled trial of interventions on human subjects (e.g., a clinical trial of a drug, or an evaluation of a consumer item such as a fragrance). In particular, non-contact or minimal-contact measurement of quality-of-life parameters such as sleep, stress, relaxation, drowsiness, temperature and emotional state of humans may be evaluated, together with automated sampling, storage, and transmission to a remote data analysis center. One component of the system is that the objective data is measured with as little disruption as possible to the normal behavior of the subject. The system can also support behavioral and pharmaceutical interventions aimed at improving quality of life."

US Application no. 20100099954 A1 outlines "System and method for a user to monitor and/or modify his or her sleep. In one embodiment, the sleep coaching system comprises a sensor for sensing a physiological signal of a sleeping user such as an EEG, computer memory databases for storing user and sleep-related data and advice, and a processor that generates a set of advice to improve user sleep satisfaction based on the user and sleep-related data. The advice to improve user sleep satisfaction, which may be communicated to the user, may comprise a sleep coaching plan, which may include one or more sleep coaching workshops that the user may undertake."

A need may therefore exist for systems that assist in the monitoring and management of fatigue in a more objective and/or personalisable way.

5 BRIEF SUMMARY OF THE TECHNOLOGY

The present technology is directed towards systems and methods for monitoring and managing fatigue.

A first aspect of the present technology relates to a fatigue monitoring and management system.

Another aspect of the present technology relates to methods for monitoring and managing fatigue.

Aspects of the present technology combine objective mental and physical "recharge" estimates derived from non-obtrusive sleep sensors, with physical activity and user data, both objective and subjective, in order to provide an assessment of fatigue.

One form of the present technology comprises a system for monitoring a user's fatigue state, the system comprising one or more data sources such as objective measures of sleep and SDB, subjective user data, objective fatigue measurements, and environmental data, and a monitoring module that analyses the data to generate an assessment of the fatigue state of the user.

The disclosed system can provide information to the user (which may prompt them to change their behaviour, or at least be aware of their level of fatigue) based on their assessed fatigue state, or to a third party in order to manage the user's activity (e.g., assign drivers or pilots based on fatigue levels). The system is thus configured to pro-actively manage a user's fatigue state.

In one example, the disclosed system acts as a personalized fatigue and sleep analyzer capable of providing a person with a personalized and scientifically valid 'go to sleep' time that will maximize sleep and minimize fatigue for better health and performance.

The following are aspects of various forms of the present technology.

1. Use of a linear model to monitor fatigue (and daytime sleepiness levels) based on the last 24, 48, 72 hours and longer past periods of objective sleep parameters, including light, deep, and REM sleep, interruptions, and to-bed and out-of-bed times.
2. A method of combining objective sleep measures with daily activity levels and calorie intake and body-mass index (BMI) to monitor fatigue (chronic or acute) to form a quality of life measure.
3. A method of combining objective sleep measures, and optionally activity and other lifestyle parameters, with subjective user data gathered via questionnaire and/or via games to estimate reaction time/vigilance as a proxy for fatigue.
4. A method of combining RPT device or radio frequency sensor-estimated AHI measures for a sleep period to a baseline AHI for a user to estimate their tiredness/fatigue, whereby the AHI is seen to increase with tiredness/fatigue (with other factors such as alcohol controlled for by user questionnaire).
5. A method of improving CPAP therapy compliance by using fatigue measurements to influence CPAP therapy compliance.
6. A method of combining snoring level and duration estimated via audio processing to a baseline snoring level for a user, whereby the snoring level is seen to increase with tiredness/fatigue (with other factors such as alcohol controlled for by user questionnaire). Snoring measures obtained from audio processing may be combined with sleep sensor data processing and other measures of sleep-disordered breathing to improve accuracy.
7. The use of default fatigue thresholds (e.g., less than 5 hours sleep leading to acute fatigue) that are subsequently modified based on the comparison of user demographic values to population values stored in a database, and further modified based on data gathered from the user over time.
8. Cognitive recharge (as estimated via REM sleep duration, and optionally via vigilance or attention games or questionnaire or prompt) is correlated with user supplied state of mind (mood) via questionnaire or prompt (e.g. via a smartphone app), and past values, in order to allow the prediction of state of mind based on future sleep parameters.
9. The comparison of objective sleep and estimated fatigue parameters with normative demographic data in order to estimate a "real sleep age", i.e., based on a user's sleep and fatigue estimates, what is the user's equivalent age (e.g., a 20 year old male with poor sleep hygiene might be classified as having a "real sleep age" of 45).
10. Objective measures of REM and deep sleep parameters from a radio frequency movement sensor or mattress-based pressure sensor, whereby deep sleep is correlated to physical recovery and REM sleep is correlated to mental (cognitive) recovery from fatigue.

Some versions of the present technology may include a system for monitoring fatigue of a user. The system may include one or more data sources. The one or more data sources may include a sleep sensor, such as a non-obtrusive sleep sensor, configured to generate objective sleep measures of the user. The system may also include a fatigue monitoring module, such as a module of a processor. The module may be configured to generate an assessment of a fatigue state of the user based on the data from the one or more data sources.

In some cases, the one or more data sources may further comprises one or more of: an activity sensor configured to generate physical activity data of the user; an environmental sensor configured to generate environmental data relating to ambient conditions in a sleep location of the user; a device configured to capture subjective user data related to the user's self-perceived fatigue state; a device configured to capture daytime vital signs data of the user; a device configured to capture objective measurements of fatigue or sleepiness of the user; a clock; and work pattern information for the user.

In some cases, the subjective user data may include lifestyle parameters comprising one or more of: caffeine intake; stress levels; energy levels; state of mind; and perceived sleep quality. Optionally, the environmental data may include one or more of season, weather, and allergy information. The environmental data may include one or more of ambient temperature, ambient audio levels, light levels, air quality, and humidity. The objective measurements of fatigue or sleepiness may be obtained from user tests. The objective measurements of fatigue or sleepiness may be obtained from game play by the user. The fatigue monitoring module may generate the assessment of the fatigue state of the user based on a historical database configured to capture data from the one or more data sources over a predetermined time window. The fatigue monitoring module may be further configured to generate the assessment of the fatigue state of the user based on baseline parameters for the user derived from trend analysis of the data in the historical database. The fatigue monitoring module may be further configured to generate the assessment of the fatigue state of the user based on a population database comprising data from the one or more data sources from multiple users of the system. The fatigue monitoring module may be further configured to generate the assessment of the fatigue state of the user based on baseline parameters for the user derived from responses to a questionnaire.

In some cases, the sleep sensor may be further configured to provide a sleep disordered breathing measure. The sleep disordered breathing measure may be a snoring measure. Optionally, the sleep sensor data may be combined with audio data from an audio sensor to obtain the snoring measure. The snoring measure may be restricted to intervals when the sleep sensor data indicates that the user is present and asleep. The sleep sensor may be a movement sensor, and obtaining the snoring measure may include detecting a snoring-like event in the audio data contemporaneously or simultaneously with a high frequency component in a respiratory movement signal from the movement sensor. In some cases, the sleep disordered breathing measure may be an apnea index, a hypopnea index and/or an apnea-hypopnea index. In some versions, the sleep disordered breathing measure may be an elevated breathing rate.

In some versions of the system, the assessment of the fatigue state of the user may include an estimate of a present fatigue state of the user. In some cases, the assessment of the fatigue state of the user may include or involve a prediction of a future fatigue state of the user at a specified time. In some versions, the objective sleep measures may include one or more of: heart rate; breathing rate; biomotion levels; sleep statistics; galvanic skin response; and body temperature. In some versions, the sleep statistics may include one or more of: duration of sleep; quality of sleep; number of interruptions of sleep; REM sleep duration; wake after sleep onset; sleep inertia; and sleep latency.

Some versions of the system may include a third party information module configured to provide information to a third party related to the assessment of the fatigue state of the user. In some cases, the system may include a user information module configured to provide information to the user related to the assessment of the fatigue state of the user.

In some cases, the sleep sensor may be a sensor integrated with a respiratory pressure therapy device from which the user may receive or is receiving CPAP therapy. In some versions, the fatigue monitoring module may be a linear classifier configured to linearly combine the data from the one or more data sources to generate a fatigue index. Optionally, the fatigue monitoring module may apply a rule set to the data from the one or more data sources to generate a fatigue index. In some cases, the fatigue index may be mapped to one of set of fatigue states. The fatigue monitoring module may be implemented on a processing device associated with the user, which may be connected to the one or more data sources. The fatigue monitoring module may be implemented at a remote server connected to the one or more data sources over a network.

Some versions of the present technology may include a method of monitoring fatigue of a user. The method may include generating, such as in one or more processors, an assessment of a fatigue state of the user based on data from one or more data sources. The data may include objective sleep measures of the user generated by a non-obtrusive sleep sensor. Optionally, the method may further involve providing the user with the fatigue state assessment, such as via an output device associated with a processor. In some cases, the method may further include generating or making a recommendation to the user based on the fatigue state assessment, such as via an output device associated with a processor. In some cases, the recommendation may be an ideal time for the user to go to sleep. In some cases, the recommendation may be an optimal time for the user to wake up. In some cases, the user may be undergoing CPAP therapy, and the recommendation may be a recommendation to improve or change the CPAP therapy. In some cases, the method may further include providing a third party with the fatigue state assessment. In some cases, the assessment generating may include applying a linear classifier to the one or more data sources. In some cases, the method may further involve, such as before the generating, applying a non-linear transformation to one or more of the data sources.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

6 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

Figure 3:
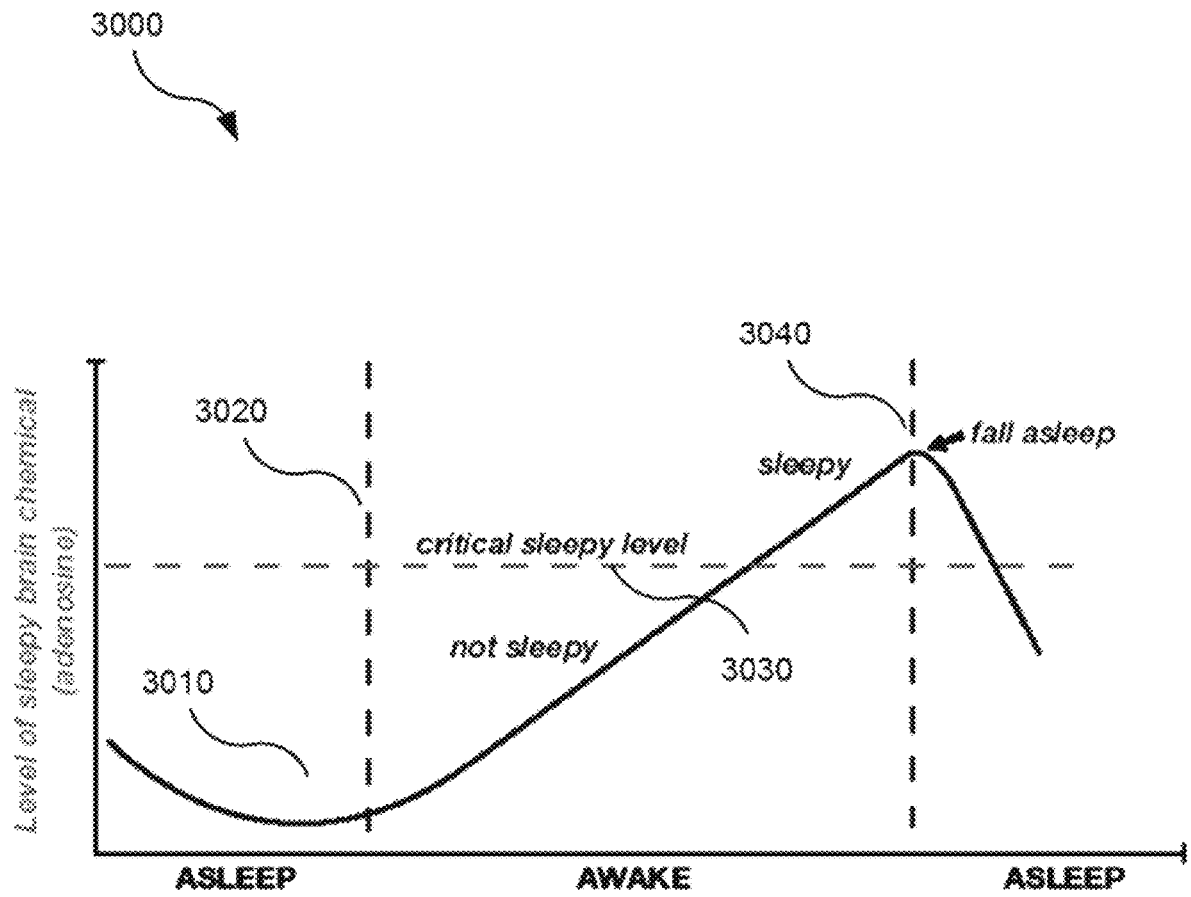

FIG. 3 contains an example graph of the level of adenosine in a person's bloodstream over a day.

Figure 1:
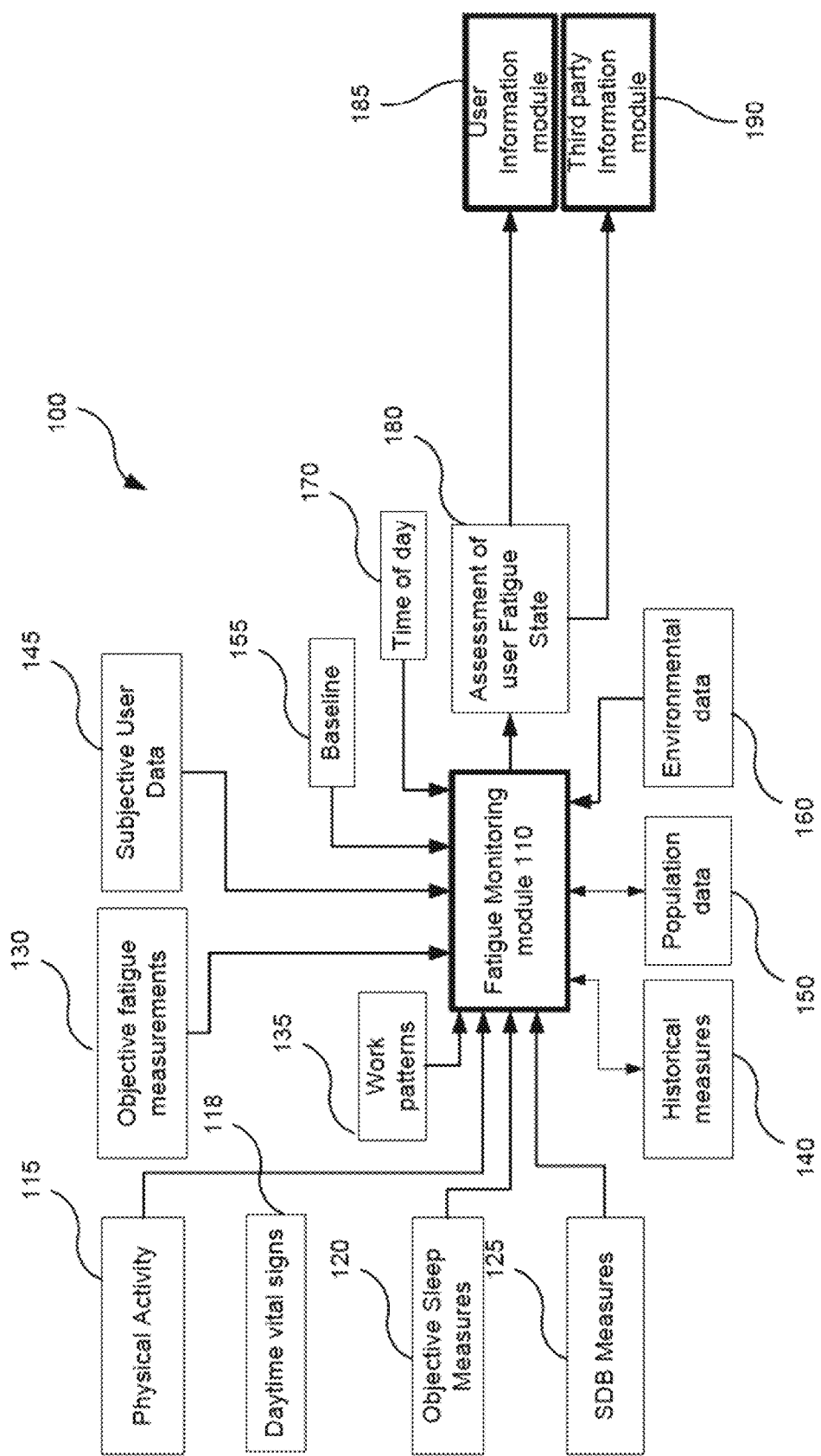
FIG. 1 is a block diagram illustrating the data flow of a fatigue monitoring and management system in accordance with one form of the present technology.
Figure 4:
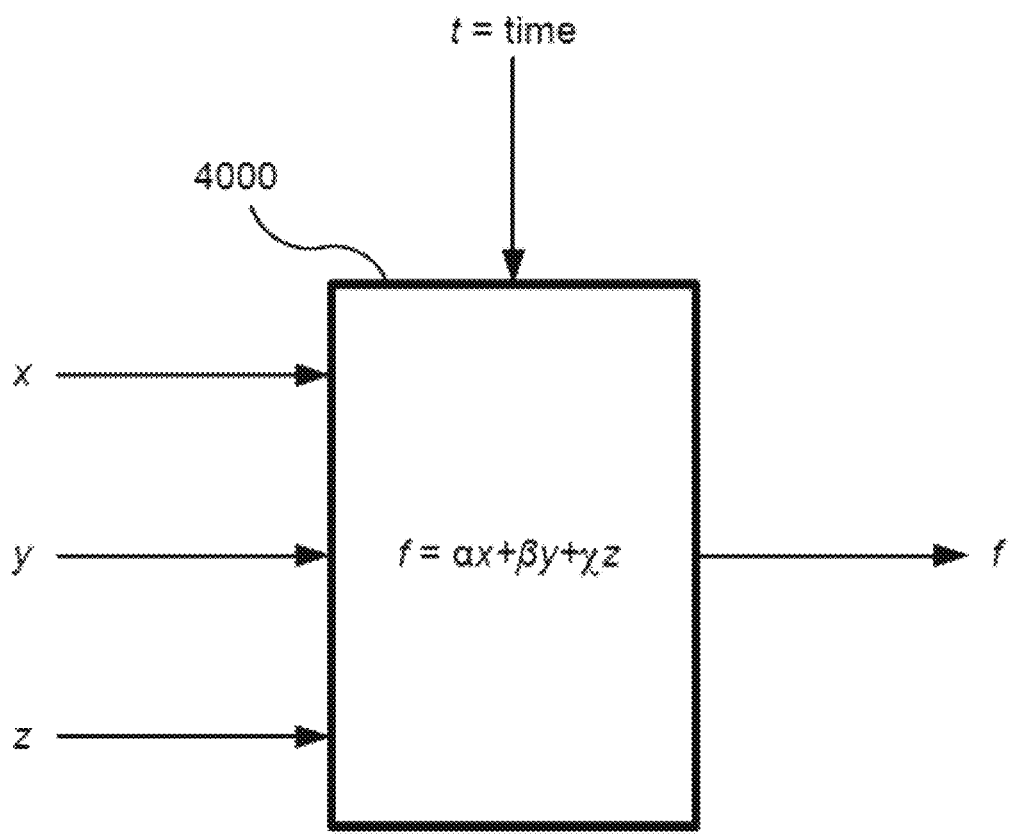

FIG. 4 is a block diagram of an example linear classifier that may be used as the fatigue monitoring module in the data flow of FIG. 1.

Figure 5:
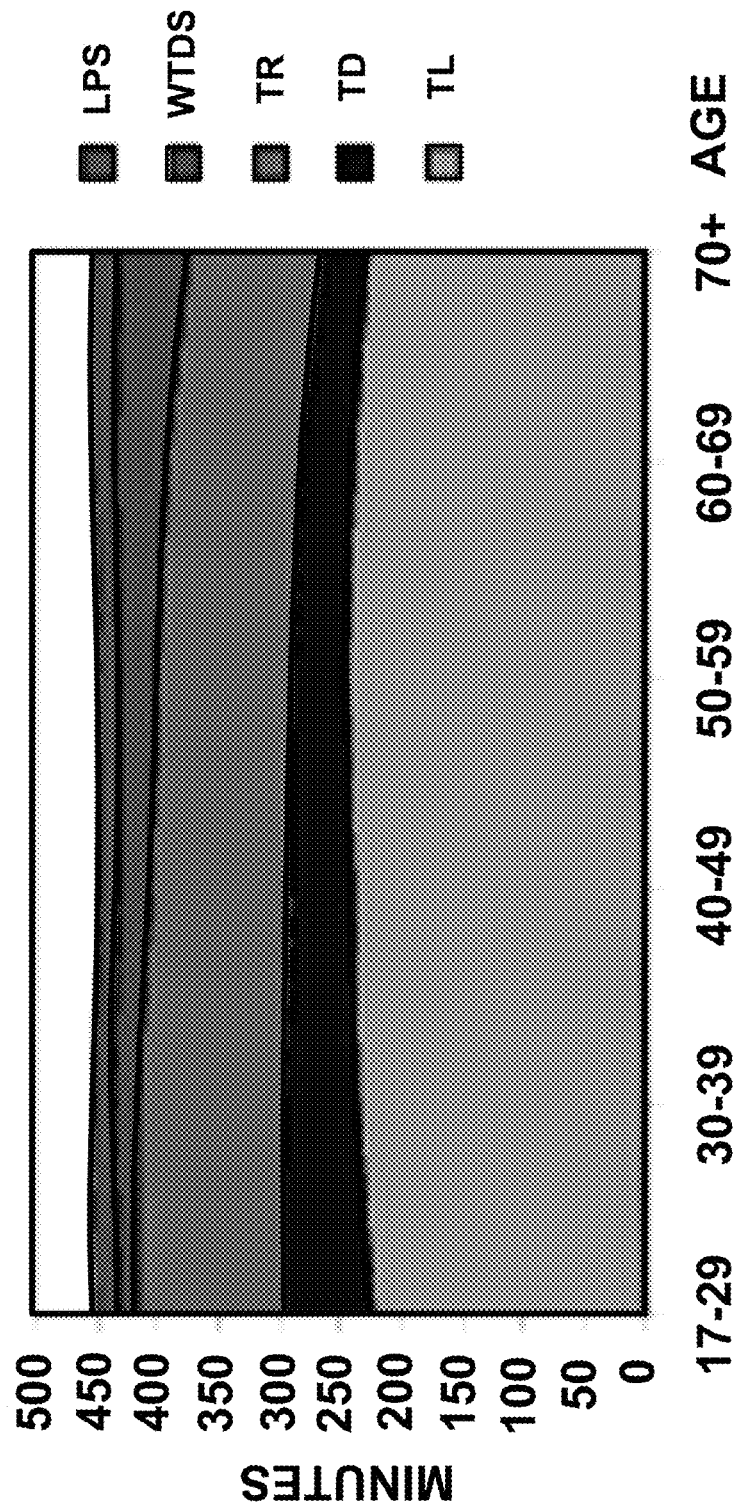

FIG. 5 is a chart representing an example distribution of sleep stages as a function of age.

Figure 6:
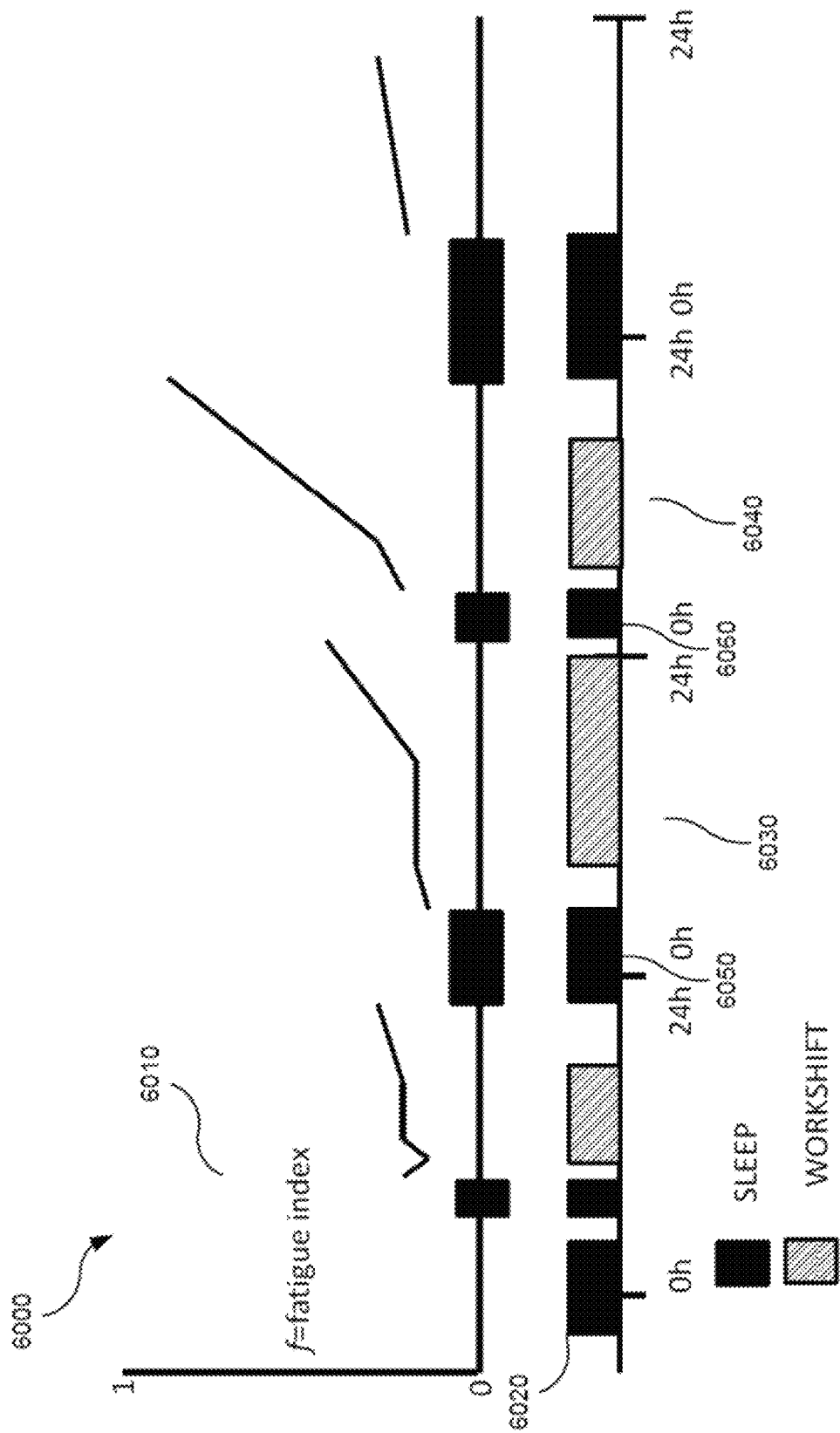

FIG. 6 contains a schematic representation of how sleep measures and work pattern data can be displayed relative to the fatigue index of an individual over several days.

Figure 7:
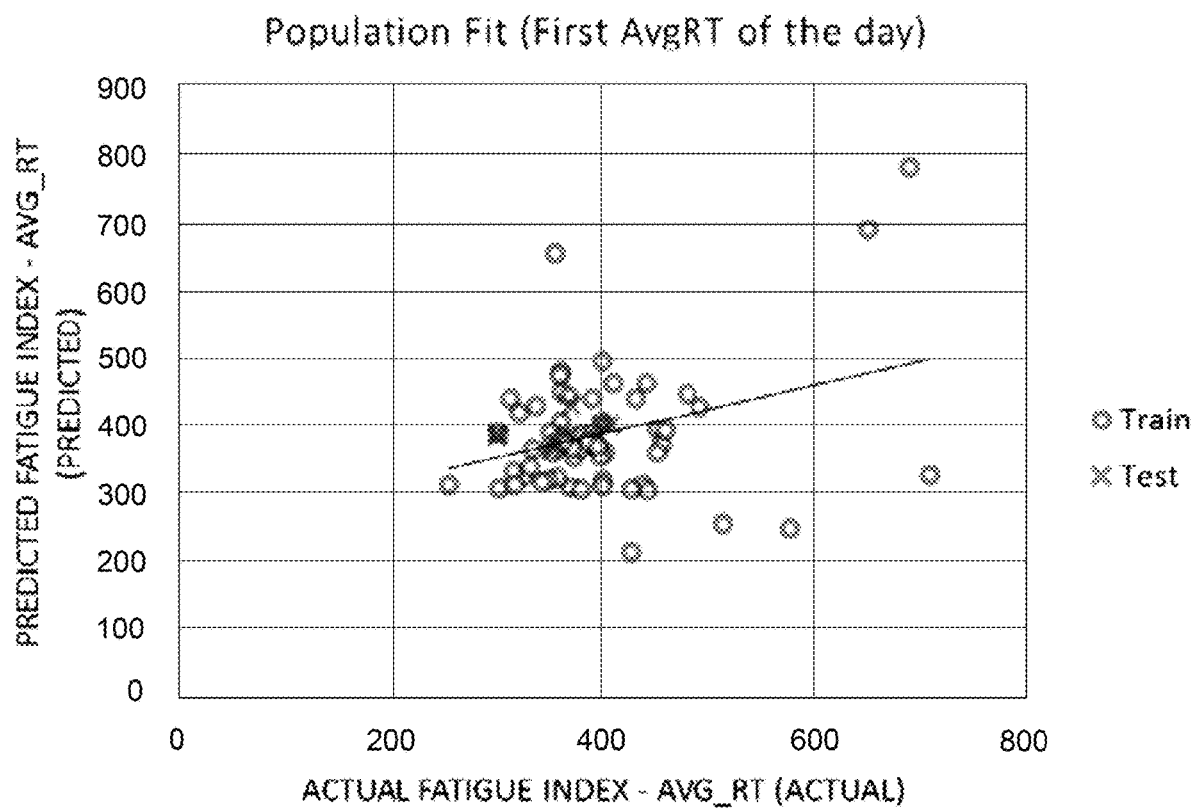

FIG. 7 contains a plot of a psychomotor vigilance test (PVT) average reaction time predictions on both training and test data against the actual PVT average reaction time (fatigue index).

7 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

7.1 Fatigue Monitoring and Management System

FIG. 1 is a block diagram illustrating the data flow of a fatigue monitoring and management system 100 in accordance with one form of the present technology. The principal processing block is a fatigue monitoring module 110. The fatigue monitoring module 110 takes input from multiple data sources (data 115 to 170) to provide an assessment 180 of the state of fatigue of a user of the fatigue monitoring and management system. The assessment 180 can take the form of an estimate of a present state of fatigue of the user, or a prediction of a future state of the fatigue of the user at a specified time instant. User information module 185 generates and provides information to the user based on the estimated or predicted fatigue state. Third party information module 190 generates and provides information to a third party based on the estimated or predicted fatigue state. The information modules 185 and 190 enable proactive management of the fatigue of the user, as described in detail below.

The fatigue model used by the fatigue monitoring and management system 100 is based on personalization, whereby the system can 'learn' user-specific sleep patterns, and relate those to subjective assessments of fatigue (how does the user "feel", e.g. according to the Karolinska Sleepiness Scale (KSS)), or to objective measurements of fatigue (e.g., performance on a Psychomotor Vigilance Test, or PVT).

The fatigue monitoring and management system 100 can be implemented in a consumer setting serving a single individual, or in a workplace setting as part of a corporate workplace fatigue management approach, optionally attached to an existing fatigue management module of an occupational health and safety system (OH&S). This enables a population management capability, utilizing de-identified (anonymous to the corporation) data. This customized corporate data represents a subset of the full population database (e.g., population data 150) used to provide normative data comparisons to the fatigue monitoring module 110.

In a consumer implementation, the fatigue monitoring module 110 may be implemented as software running on a processing device associated with the user such as a personal or laptop computer, mobile telephone, smartphone, or tablet computer, connected in wired or wireless fashion to one or more of the various data sources (data 115 to 170), which may optionally include, be coupled with, or communicate with one or more sensors to detect or generate signals from which the data (as discussed in more detail herein) may be derived. Sleepiness, sleep health and cognitive performance questionnaires (as used to obtain subjective user data 145) may be completed by the user on the same processing device. The user information module 185 may then provide information to the user via the same processing device.

Alternatively, the fatigue monitoring module 110 can be implemented "in the cloud", i.e. at a remote server connected to the various data sources (data 115 to 170) over a network. This enables fatigue state data from multiple individuals to be aggregated, as in a workplace implementation. However, a consumer implementation may also utilise a "cloud-based" fatigue monitoring module. The remote server can forward, via the network, sleepiness, sleep health and cognitive performance questionnaires (as used to obtain subjective user data 145) to each individual, and each individual may complete such, using a networked device such as a personal or laptop computer, mobile telephone, smartphone, or tablet computer. The user information module 185 can then provide information to each individual via the same device. The third party information module 190 can provide information to a third party, such as a corporate officer, via the network.

The various data sources (data 115 to 170) used by the fatigue monitoring module 110 are described in detail below. In various forms of the present technology, some subset of the data sources (data 115 to 170) are used by the fatigue monitoring module 110 to produce the estimated or predicted fatigue state 180.

Thus, the methodologies described herein may be implemented within/by one or more processing devices. For example, as described herein, data source and/or module embodiments of the present technology may be a processing device that may have one or more processors to implement the particular methodologies or algorithms described in more detail herein. Such a device or apparatus may include integrated chips, a memory and/or other control instruction, data or information storage medium. For example, programmed instructions encompassing such methodologies may be coded on integrated chips in the memory of the device or apparatus to form an application specific integrated chip (ASIC). Such instructions may also or alternatively be loaded as software or firmware using an appropriate data storage medium. Such processing devices may optionally be further in communication or coupled with input devices, such as keyboards, touch screens, sensors, etc.

In what follows, it is generally assumed that a person sleeps during the night and is awake during the day, so "day" is used synonymously with "waking period" and "night" with "sleeping period". However, the disclosed fatigue monitoring and management system 100 is also contemplated for use by shift workers whose sleep and waking periods may not coincide with nights and days respectively. For such users, "day" may be still understood to indicate "waking period" and "night" to indicate "sleeping period" even through the true correspondences may be more like the reverse.

7.1.1 Physical Activity (Data 115)

Increased fatigue is associated with reduced exercise and activity. The physical activity data 115 may be obtained from wearable activity sensors (e.g., pedometers, "step counters", actigraphs based on triaxial accelerometers, altimeters, and branded commercial activity sensors such as "Fitbit", "Jawbone Up", and "Actiwatch"). Alternatively, physical activity data 115 may be obtained from portable devices such as smartphones incorporating activity sensors. Examples of physical activity data are the number of steps taken and duration and intensity of exercise. The physical activity data 115 is used to build up a profile of the daily activity levels of the user.

7.1.2 Daytime Vital Signs (Data 118)

Fatigue may be related to daytime stress levels. The daytime dynamics of physiological vital signs such as heart rate, breathing rate, and blood pressure may be gathered by wearable devices such as Polar heart rate chest band, ECG/R-peak or other data collection devices attached to the chest, or by ear buds (ear phones) that record these signals using photoplethysmographic (PPG) methods (e.g., made by LG or Blaupunkt). In one implementation, blood pressure estimates from ear bud sensors may be used to non-invasively track blood pressure values during the day (e.g., when the user is listening to music/commuting/exercising and so forth).

Heart rate estimates may also be combined with daytime physical activity data 115 in order to produce an estimate of energy expenditure.

Detecting trend changes in heart rate may be indicative of increased fatigue, for example in athletes overtraining.

Chronic stress may also manifest in daytime fatigue, and may be monitored based on daytime physical activity data 115, daytime vital signs data 118, and objective sleep measures 120 (described below).

Other chronic conditions such as chronic disease progression may manifest in changes in daytime vital signs data 118, such as increased heart rate, decreased heart rate variability, increased breathing rate, changes in blood pressure, and decreased energy expenditure.

Jackowska et al. (2012) found that sleep problems may be associated with reduced daytime heart rate variability (HRV). Therefore, in a holistic view of fatigue, the impact of fatigue can be weighted based on both nightly sleep patterns (e.g., fragmented/poor sleep) followed by estimates of HRV during the next day. Where the daytime impact is increased, the cumulative impact of fatigue may be increasing.

7.1.3 Objective Sleep Measures 120

Figure 2:
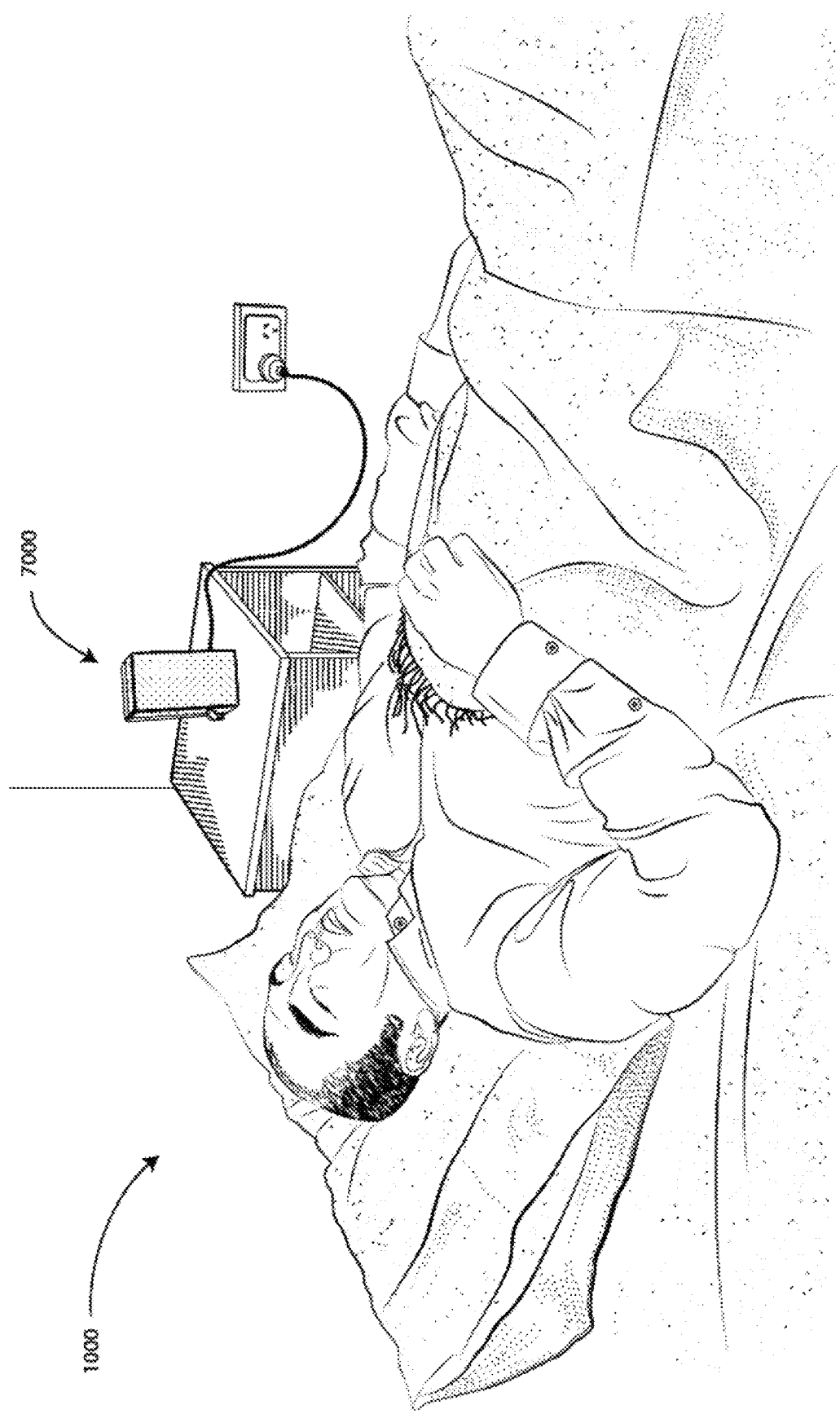
FIG. 2 shows a person asleep in bed being monitored by an example non-contact sensor.

"Sleep sensors" that monitor a user's sleep and breathing may be utilised to provide objective sleep measures 120 such as daily and longitudinal trending of objective sleep quality and biomotion levels in the bedroom or other sleep location. Advantageously, the objective sleep measures 120 are extracted from sleep sensors with minimal or no obtrusiveness to the user. Non-obtrusive sleep sensor technologies do not require to be worn, i.e. they are 'set and forget', so as to maximize long-term usage. One example of a non-obtrusive sleep sensor is a non-contact sensor. FIG. 2 illustrates a person 1000 asleep in bed being monitored by an example non-contact sensor 7000, which may be a radio-frequency Doppler movement sensor (SleepMinder).

Another example of a non-obtrusive sleep sensor is a mattress-based capacitive or resistive mat (including piezo-electric) pressure sensor.

In implementations in which a user is receiving CPAP therapy for obstructive sleep apnea from an RPT device via a patient interface such as a mask, the sleep sensors may be the sensors integrated with the RPT device or patient interface, such as pressure or flow rate sensors.

Objective sleep measures 120 extracted from the sleep sensor signal(s) may include sleep statistics such as the duration of sleep, quality of sleep (amount of actual sleep during the expected sleep period), and the number of interruptions of sleep. The time-to-bed as well as wake-up time may also be extracted from the sleep sensor signal(s). REM sleep periods may also be extracted, along with deep sleep (slow wave sleep) periods. As mentioned above, REM sleep duration indicates cognitive recharge, while deep sleep duration indicates physical recharge. The relative ratios of deep sleep, light sleep, and REM sleep duration may also be extracted. Another sleep statistic is sleep inertia, representing the expected tiredness level immediately following waking up, particularly in the case where a user wakes directly from deep sleep. Wake after sleep onset (WASO) provides an aggregated estimate of fragmented sleep, which may be used in conjunction with the number of interruptions detected. Time to sleep (sleep latency) and sleep stage upon waking may also be extracted.

Where the sleep sensor has the capability to measure heart rate, e.g., RF Doppler movement sensors or mattress-based pressure sensors monitoring the ballistocardiogram, power spectral analysis may be performed on the signal to reveal variability of inter-cardiac intervals that may be predictive of fatigue. In particular, the ratio of HF (high frequency) to LF (low frequency) power in the heart rate spectrum may be used to estimate the parasympathetic nervous activity, with reduced parasympathetic component (of the autonomic nervous system) suggesting increased stress level and increased fatigue. Particularly, sympathetic nervous system (fight or flight response) activation in chronic fatigue can manifest just when the body should be recovering, i.e., during sleep. Heart rate data (and thus HRV) can also be obtained from contact sensors such as wearable wrist watch-style devices with optical sensors, pulse oximeters, chest straps such as the Polar heart rate monitor, or headbands with EEG electrodes for example.

Galvanic skin response (GSR, also known as electrodermal response) can be recorded by a wearable device (e.g., the Basis watch, or other commercially available GSR measurement devices). The GSR signal may be used as a surrogate measure of sympathetic nervous system "fight or flight" activation. Combining the extracted GSR and HRV signals can also yield an estimate of the ratio between sympathetic and parasympathetic nervous system activation.

HRV and GSR data may also be gathered when the user is awake (e.g. via chest electrodes or a wrist watch-style device), in which case they form part of the daytime vital signs data 118.

Methods for extracting objective sleep measures 120 such as biomotion levels, breathing rate, heart rate, and sleep statistics from a non-contact radio frequency Doppler movement sensor signal are outlined in PCT publication no. WO 2010/091168, for example, the entire contents of which are herein incorporated by reference.

A specific example of a sleep sensor is a piezo-resistive over-mattress band based on graphene (a crystalline form of carbon)-impregnated rubber (or other conductive materials with a plastic or rubber covering) with an electronic buffer, amplification and digitizing circuit.

In the case where the objective sleep measures 120 appear to be worse than the subjective user data 145, comparison to other lifestyle parameters as well as SDB measures 125 may be performed.

A further objective measure 120 of actual sleep quality which may affect fatigue level is surface body temperature (calibrated for ambient temperature). For example, such a temperature monitoring device might be embodied as the BodyMedia Sensewear device which incorporates two sensors to measure ambient and skin temperature, and hence to provide corrections for underlying body temperature. Body temperature is important for assessment of sleep quality as there is a characteristic temperature pattern throughout a normal night of sleep. Promoters of fatigue (such as jetlag) will tend to cause deviations from this pattern as the sleep temperature profile is "over-ridden" by the underlying circadian variation of body temperature. Hence, a potential contributing objective sleep measure 120 can be the estimated body temperature throughout the night, and the variations of this temperature profile from the expected profile for that user.

7.1.4 SDB Measures 125

In addition to poor sleep hygiene (such as self-imposed sleep restrictions), a major contributor to fatigue is the presence of sleep-disordered breathing (SDB). Examples of SDB measures 125 are the apnea-hypopnea index (AHI) and the incidence and severity of periodic limb movement (PLM). Methods for extracting SDB measures such as AHI from a non-contact radio frequency Doppler movement sensor signal are outlined in PCT publication no. WO 2010/091168, for example, the contents of which are herein incorporated by reference.

Another SDB measure 125 is elevated breathing rate, e.g., median breathing rate during sleep being over 20 to 24 breaths per minute (depending on age and underlying condition).

Additionally, snoring is an SDB measure 125 that may be quantified based on short time Fourier transform (STFT) analysis of a sampled audio waveform obtained from an audio sensor, and estimation of normalized sub-band power levels thereof. Mel-frequency cepstral coefficients (MFCCs) may be used to distinguish snoring from speech, and spectral flux (analyzing changes between power spectral estimates) may be used to detect the onset of snoring. RMS (root mean square, or the quadratic mean) may be used in conjunction with the STFT power levels and a running median filter to distinguish triggering sound levels from background noise.

Snoring (and cessation of snoring related to apnea or hypopnea events) may be combined with biomotion levels and extracted sleep statistics in the following manner. A smartphone may be placed on a bedside table on the side of the bed that the subject usually sleeps on. A generic audio logger (voice memo) smartphone app may be used to save audio files from the inbuilt audio sensor (microphone) to memory. In order to minimise temporary storage space, audio may be sampled at 11.025 kHz, mono (single channel). Otherwise 22.5 kHz or 44.1 kHz (or other sampling rates) may be used. Preferably, audio should be sampled at the highest rate available; the sampled signal may be downsampled later. (Some internal smartphone microphones set an upper sampling rate limit of 8 kHz.) It is also preferable that the microphone is facing the user. For example, a Samsung Galaxy S3 has two microphones, with the "voice recording" microphone being a pinhole on the lower right hand edge. An Apple iphone 5 also has two microphones, with the voice recording microphone being on the bottom left hand edge. Note that some iPod variants require the accessory headphones/microphone to be connected to be able to record (e.g., older than Gen 4 iPod Touch).

For ease of processing, the audio data may be read in blocks from the input file. This block size may be configurable, and represents a trade-off between memory i/o speed, and available memory. Ten to twenty minute segments are an example block size. Signal pre-processing can involve applying a digital bandpass filter, retaining frequency content in the range 100 Hz to 4,000 Hz. This may be archived by using a direct form FIR filter using a Kaiser window or by other means. The signal may be resampled to 8000 Hz (if storage space limitations require this). Optionally, the signal may be companded—for example, by applying a u-law compressor or similar approach. This may also be managed by other signal processing means, and companding is not necessarily required.

In the frequency domain, features can include sub-band powers in the following sub-bands (in Hz): 0.01-500, 500-1000, 1000-1500, 1500-2000, 2000-2500. For higher sampling rates, higher frequency bands may be considered. The frequency bands may also be split into smaller or larger segments. For example, a specific sub-band below 800 Hz may be considered—i.e., 0-800 Hz (de-meaned). Other spectral measures are the spectral centroid, and audio processing steps such as 'pitch'—the harmonic product spectrum, spectral flux, spectral spread, spectral autocorrelation coefficients, and/or spectral kurtosis. For example, the ratio of power greater than 800 Hz to that less than 800 Hz could distinguish simple snorers from those with SDB (where the specific separating frequency is empirically selected based on the snoring population).

Visually, it is possible to track "lines" at snoring frequency in a spectrogram (STFT-based). Therefore, it is possible to use automatic algorithmic approaches to detect and extract these "lines" based on techniques used in military sonar applications and similar, including hidden Markov models and image tracking techniques.

In the time domain, features can include zero crossing rate, autocorrelation coefficients, and running amplitude measures. Other approaches are to calculate the short term energy and short-time zero crossing rate.

A common problem with snore detection from audio signals is corruption from background noise—i.e., noise sources that do not originate from the user being monitored. These sources may include white noise or other coloured noise-style sources (e.g., fans, air conditioning, road hum), voice, music etc. from TV, radio, smartphone (e.g., user watching a movie on a tablet), another person in the room talking, or indeed another person snoring (e.g., bed partner). By advanced audio processing, and also by combining audio processing with sleep sensor data processing (including absence/presence, wake, and sleep stage detection), this problem may be addressed.

If the user is playing audio/media on the same smartphone on which the snoring detection is implemented (or on a connected or networked device), it is possible to exclude non-snoring components, i.e., to exclude those sounds that are not snoring in origin. For audio/media being played—or other speech sources, e.g., a conversation in the room—a voice recognition system (e.g., based on vocoders) can be used to scan the audio source recorded. For this application, a recognition of voice features is used to suppress snoring detection—the assumption being that snoring only occurs when other speech sources are not present. This poses a problem when the user falls asleep with the radio or TV turned on; however, this problem can be addressed by using sleep stages detected by a separate sleep sensor (i.e., specifically restrict snoring detection to intervals when (a) the user is present, and (b) when the user is asleep).

By combining the audio processing and sleep sensor data processing (including absence/presence and sleep staging), it is possible to restrict snoring detection to when the nearest user to the audio sensor is asleep. Therefore, even if the bed partner is snoring, but the monitored user is awake, these snoring episodes are excluded. This will also have the effect of excluding snoring when the user gets out of bed (e.g., to go to the toilet) as they are detected as awake, and then out of range (absent) by the sleep sensor.

A confounding factor remains, in that both bed partners may be asleep, and both snoring (or only the further away (unmonitored) user is snoring—with both asleep). In this case (or other cases), access to the respiratory movement signal from a movement sensor may be combined with detected snoring-like events from the audio signal. For example, an audio snoring event may be correlated with a high frequency component overlaid on the respiratory movement signal—e.g. as a high frequency component on the inspiratory phase. In other snoring types, snoring may occur on both inspiratory and expiratory phases. These snoring patterns in respiratory movement data may be dependent on the positioning of the movement sensor. Detection of apnea and hypopnea events from the respiratory movement signal may also be correlated with changes in detected snoring patterns. A further advantage of the simultaneous acquisition of snoring audio signals and vibrations from a movement sensor, is that since snoring is much more common during inspiration, the snoring may be used to decide whether a movement signal represents inspiration or expiration. A further clue can be obtained by evaluating the inspiration to expiration ratio (which is typically 1:2 in normal subjects).

Snoring events can also be correlated to sleep stages, e.g., occurrences in non-REM versus REM sleep periods. While conventional snore may be more prevalent in deep sleep and light sleep, less may be seen in REM sleep. REM sleep may contain different audio events, such as those related to recovery breaths from apnea (for example).

Another means of detecting snoring from a specific user—and indeed providing a refined estimate of their breathing rate—is to compare breathing rate estimates extracted from audio signals and from movement signals. Where these are closely correlated, it is likely that the nearest user is detected. Where these both remain high quality but separated in value, it may be that a further user has been detected. Where the audio signal contains significant snoring (or the audio quality is very poor), a breathing rate estimate may not be possible from the audio signal, and no correlation can be performed between the signals in this manner.

7.1.5 Objective Fatigue Measurements 130

An important aspect of the disclosed fatigue monitoring and management system 100 is that it may incorporate accepted objective measurements of sleepiness or fatigue 130, e.g. those obtained from user tests. Generally, tests used to obtain the objective fatigue measurements 130 address cognitive, executive function, stress, and energy levels, all of which are affected by fatigue. Formal user tests that may be used to obtain the objective fatigue measurements 130 include a psychomotor vigilance test (PVT), Osler (Oxford Sleep Resistance test), and maintenance of wakefulness test (MWT). A PVT evaluates reaction times and hand/eye coordination. A PVT test is a reasonably well accepted measurement of one type of attention, which has been shown previously to act as a reasonable indicator of sleepiness, which is a known correlative of fatigue. In one example of a PVT, a light is presented to a user via a handheld device at random times, to which the user must respond by pressing a button. Metrics provided by a PVT include average or median reaction time and number of misses. In another example of a PVT, a user must follow a target and maintain their position. A Sustained Attention Response Test is another method of measuring sleepiness.

In one implementation, a PVT may be undertaken four times a day (e.g. two hours after getting up, one hour after lunch, thirty minutes after dinner, and one hour before bed).

Other types of tests both induce mental fatigue and assess its level. For example, the computerized Kraepelin test is one way to induce a mental fatigue load. In this test, the user is asked to repeat mental arithmetic and selection tests repeatedly over prolonged times (e.g., 1-2 hrs). The task itself has been shown to induce fatigue, and this can be assessed by looking at the speed (plus variability of speed) of the arithmetic, and the accuracy of the answers.

A further objective way to quantify fatigue during waking hours is to use an EEG measurement of fatigue. A number of EEG predictors of fatigue have been evaluated such as those described by Trejo et al.

In one implementation of the disclosed fatigue monitoring system (e.g., system 100), a user wears an EEG headband during a training phase of the system to provide objective measurements of fatigue 130. These measures are used to train the model relating the measured objective and subjective user data, and the actual fatigue experienced by that user.

These types of tests may be incorporated into the fatigue monitoring and management system 100 to provide objective measurements of sleepiness or fatigue 130 (and hence act as internal "calibration" points of fatigue).

The objective fatigue measurements 130 may be "hard" measures from more formal sustained attention tests such as those described above, or "soft" measures that are derived from game play. Regarding the latter alternative, attention testing can be "gamified" to maintain engagement. Gamification is the use of game thinking and game mechanics in a non-game context to engage users and solve problems (Zichermann & Cunningham, 2011). Specifically, gamification of attention testing enables both a social aspect, and also a goal-seeking aspect. The social aspect allows population segment comparisons, e.g., "my sleep" versus that of other employees, people my own age, top performers and so forth. It also allows the sharing of these comparisons on social media sites, such as Twitter and Facebook. The goal-seeking aspect adds the concept of goals and rewards, either via an in-app "well done" message via point accumulation, or via a tangible award via the corporate sponsor of the system. Data from game play (e.g. cognitive, vigilance, and executive function estimates) can provide estimates of neuro-behavioural performance. These relate to memory, mistakes made (e.g., missing a game "goal"), and mental and physical reaction times.

8.1.6 Work Patterns (Data 135)

The fatigue monitoring and management system 100 can gain more insight if it is supplied with work pattern information 135, which could be a simple as "working a five day week, 8:30 a.m.-5 p.m.", or as complex as a detailed shift roster. The work pattern information 135 may indicate the likely sleep patterns of a user, and increase the accuracy of a fatigue state estimate 180.

In one example, the ratio of sleep during the day to sleep at night may be extracted as part of the objective sleep measures 120. This ratio can vary based on naps taken, shift work, jet lag and other factors. Specifically, if the fatigue monitoring and management system is provided with work pattern information 135 on upcoming work hours (e.g., shift work) or travel across multiple time zones, it can allow for "anticipatory" sleep by the user as they prepare for the upcoming change (e.g., if a user deliberately varies their sleep habits in anticipation of the change in sleeping time).

8.1.7 Historical Measures 140

The fatigue monitoring module 110 can utilize historical information (e.g., historical measures 140) from the other data sources (data 115 to 170). For example, the most recent 1-7 days may provide useful information on the likely fatigue state of the user. For example, for a user with a typical observed sleep time of 7.5 hours, a gradual transition to 6 hours per night can indicate cumulative fatigue. A sudden change to 5 hours or less per night (i.e., over a short period) can be indicative of acute fatigue.

The history of each parameter from the other data sources over a predetermined time window, e.g. 7 days, may be stored in a database of historical measures 140.

8.1.8 Subjective User Data 145

The subjective user data 145 represents user-entered data, for example in response to a questionnaire. One form of subjective user data 145 relates to the user's subjective or self-perceived sleepiness. For example, the Epworth sleepiness scale (ESS) and Stanford sleepiness scale (SSS), both of which are based on questionnaires, subjectively quantify sleepiness. The Stop-Bang assessment questionnaire can provide an estimate of riskiness for SDB.

The Karolinska Sleepiness Scale (KSS) was developed as, and has been widely used as, an indicator of subjective sleepiness. The KSS asks the person to rate their sleepiness at that point in time according to the following five-point scale:

1=extremely alert
3=alert
5=neither alert nor sleepy
7=sleepy, but no difficulty staying awake
9=extremely sleepy, fighting off sleep The subjective user data 145 may be captured via a user device such as a smartphone or tablet. In one example, a smartphone "app" offers a "fatigue button" that a user activates when they feel tired/fatigued (e.g., when yawning), and optionally can allow them to select the severity of their perceived fatigue via an associated counter. In another example, known as a Visual Analog Scale (VAS), rather than asking the user to rate themselves against verbal statements, the app provides a continuum of sleepiness along which the user moves a "slider" (e.g., in a graphical user interface (GUI)) to indicate their subjective level of sleepiness.

In one implementation, a VAS may be administered four times a day (e.g., automatically triggered by a processor) (e.g. two hours after getting up, one hour after lunch, thirty minutes after dinner, and one hour before bed).

Other forms of subjective user data 145 related to perceived fatigue are lifestyle parameters such as caffeine intake, stress levels, energy levels, state of mind (mood), perceived sleep quality, and menstrual cycle, with its likelihood of associated fatigue. Each of these lifestyle parameters may be captured via a user device as described above and used as an input to the fatigue monitoring module 110.

8.1.9 Population Data 150

An aspect of the disclosed fatigue monitoring and management system 100 is that analytics can be used to compare a user's records with a larger population of records, to establish norms and also to determine where a user may fit within a population. For example, some individuals will be more susceptible to short-term sleep loss than others, and this can be learnt by examining the person's record over time. At a high level, certain regions may exhibit different fatigue characteristics, e.g., related to indigenous industry, short-term effects due to a time change, regional eating habits and BMI, socio-economic levels, seasonal effects such as duration of daylight hours, prevalence of diabetes, and so forth.

To this end, the population data 150 comprises parameters from multiple users of the fatigue monitoring and management system 100. Population data 150 can enable a preliminary assessment of fatigue states, making use of data from similar users based on a mixture of demographic, psychographic, behavioral and geographic parameters. In order to allow a comparison to normative measures, the population data 150 may be de-identified to preserve the privacy of the user.

8.1.10 Baseline (Data 155)

The baseline parameters 155 represent the normative values for a user, and may be derived from trend analysis of historical measures 140 (initially over a short time scale, but possibly extending to a view of weeks, months or years of data).

A baseline may also be established from responses to a questionnaire such as the Pittsburgh Sleep Questionnaire (PSQ) and the Quality of Life (QoL) Survey. The questionnaire may be administered and the responses 155 captured via a user device such as a smartphone or tablet.

8.1.11 Environmental (Data 160)

The local environment of the user can play a part in their fatigue levels, especially if they are sensitive to pollen count or light levels (e.g., seasonal affective disorder). Broad-scale environmental data 160 such as season, weather, and allergy information can be gathered based on the user's sleep location (either supplied by them in profile details, or obtained via geolocation devices, e.g. GPS devices), and cross-checking of appropriate online databases.

More specific environmental data 160 includes the ambient temperature of the sleeping place of the user (correlated with comfortable sleep temperatures), ambient audio levels (to detect loud noises), light levels (to identify sunrise time, cross-checked with seasonal information and location, and light control in the room), air quality, and humidity. Such data these can be obtained from dedicated calibrated environmental sensors, such as the Onset HOBO, which logs temperature values, or by smartphone environmental (e.g. ambient audio) sensors, located in-room with the user.

8.1.12 Time of Day (Data 170)

The time of day data 170, obtained from a clock, may be used as a key lookup measure in the assessment of fatigue. Time of day data 170 can capture the underlying diurnal or circadian variation of fatigue, e.g. using a sinusoidal model.

8.1.13 Other Data Inputs

Some implementations of the fatigue monitoring and management system 100 incorporate accepted physiological measurements of sleepiness and alertness such as levels of adenosine and melatonin in the bloodstream as potential calibration points for the overall sleepiness level of the user. Adenosine level is indicative of sleepiness because adenosine slows down nerve activity. FIG. 3 contains an example graph 3000 of a level of adenosine in a person's bloodstream over a day. In the first section 3010 the level is low while the person is asleep. The level starts to rise just before the person awakes at time 3020, and continues to rise throughout the waking period until it exceeds a "critical sleepy level" 3030 at which point the person is sleepy. The person falls asleep at time 3040, after which the level begins to fall. Note that caffeine can provide a short-term boost to alertness levels by binding preferentially with adenosine receptors in the brain, and hence slowing down the nerve-inhibition effect of adenosine.

The fatigue monitoring and management system 100 may also gather information from the user on conditions/disease states that are related to fatigue, including anxiety, headache and nasal congestion, asthma, anemia (e.g., related to menstruation), depression, arthritis, diabetes, and sleep apnea.

Another type of data that may be used by the fatigue monitoring module 110 is information about bedding, e.g., type of sheets, when they were last changed, age of mattress and comforter, and presence of dust allergies. These data may be combined with their estimated fatigue pattern, sleep trends (especially quantity of movement), the room environmental data 160 (e.g., temperature) and population data 150.

In a driving implementation of the fatigue monitoring and management system 100, information related to a user's driving may be obtained via an accelerometer and geolocation device (e.g. GPS-based) in order to distinguish between driving and moving (i.e., distinguish driving from other types of movement). These data could be used to index a mapping database containing the local road network, in particular known "black spots" of fatigue-related accidents, e.g., areas or roads known to have an elevated incidence of "asleep at the wheel" accidents or fatalities.

8.1.14 Fatigue Monitoring Module 110

As mentioned above, the fatigue monitoring module 110 takes input from one or more of the data sources (data 115 to 170) to generate an assessment 180 of the fatigue state of the user. The fatigue state assessment 180 can take the form of an estimate of a present fatigue state of the user, or a prediction of a future fatigue state of the user.

The input data may undergo a non-linear transformation such as a logarithm before being used by the fatigue monitoring module 110. The input data may also be normalised, e.g. by subtraction of the mean, to remove "static bias" between individuals.

FIG. 4 is a block diagram of a linear classifier 4000 that may be used to implement the fatigue monitoring module 110 according to one form of the present technology. In FIG. 4, the linear classifier 4000 takes three data parameters x, y, and z, drawn from the input data sources (data 115 to 170), and combines them linearly with coefficients $\alpha$, $\beta$, and $\gamma$ respectively to generate a numeric "fatigue index" f. In one example, a fatigue index value of 1 indicates a high level of fatigue, and a value of 0 indicates a low level of fatigue. In other implementations, a number of input parameters greater than or less than three are linearly combined by the linear classifier 4000 to generate the fatigue index f.

A further input to the linear classifier 4000 may be the time/to which the fatigue index f is to correspond. If the time/is the present, the fatigue index f is an estimate of a present fatigue state. If the time/is a future time, the fatigue index f represents a prediction of a fatigue state at time t. The coefficients $\alpha$, $\beta$, and $\gamma$ in general vary with time, so the time/may be used to obtain the correct values of coefficients $\alpha$, $\beta$, and $\gamma$ for the assessment of fatigue.

In one example, the input parameters to the linear classifier 4000 comprise the following set of parameters: {time since wake, duration of last night's sleep, number of interruptions in previous night, running average of last five nights' sleep durations, age, gender, duration of deep sleep in previous night, room temperature last night}.

For a linear classifier 4000 to be useful, it needs appropriate values of the weighting coefficients α, β, and γ, and the "best" set of input parameters to characterize a given individual (e.g., for some individuals the most important input parameter is time since wake, for others it might be duration of last night's sleep). Multiple linear regression is a supervised way to establish the "best" set of input parameters and corresponding coefficients from a training set. In a multiple linear regression approach, the fatigue monitoring and management system 100 learns the "best" set of input parameters and corresponding coefficients to estimate or predict the fatigue state of a person. In the absence of any prior learning data, a standard linear model could be used to initialize the linear classifier 4000.

The training data could be obtained from an individual user, in which case the classifier is specific to that user, or from multiple individuals, in which case the classifier is more generic. Such a generic classifier could comprise sub-models based on training data from different regions. A generic classifier is able to make fatigue assessments based on data from a previously unknown individual.

In the situation where training data is available, this will often include objective or subjective measurements of fatigue acquired from the user during the day (using for example the psychomotor vigilance test, a Visual Analog Scale, or an EEG-based measure of fatigue). This will then allow the fitting of the linear model to a useful output fatigue index.

There are many alternatives to linear regression such as logistic regression and non-linear regression which the fatigue monitoring module 110 could use to learn the "best" set of input parameters and corresponding coefficients to estimate the fatigue index f.

In other forms of the disclosed fatigue monitoring and management system 100, the fatigue monitoring module 110 could use different approaches to generating the fatigue state assessment 180, such as non-linear classifiers, support vector machines, or neural networks.

Another implementation of the fatigue monitoring module 110 uses a rule-based approach to generate a fatigue index. One example of such an implementation comprises the following rule set having any one, more or all of the following:

If hours asleep <6, increase fatigue index [note: sometimes very short sleep may take one day to impact the user, especially if they have been OK to date; but if it persists, then they probably have chronic fatigue].

If hours asleep >10, increase fatigue index.

If to-bed time has varied by more than 2.5 hrs over the last three nights, increase fatigue index.

If deep sleep <7%, increase fatigue index.

If decrease in deep sleep vs mean of last three nights >8%, increase fatigue index. (If the decrease trend continues on a second or subsequent night, further increase fatigue index. If subsequent increase in deep sleep >5% then user is "on the mend" and fatigue index decreases.)

If REM is very short (<5 to 7%), increase fatigue index.

If sleep efficiency <75-80%, increase fatigue index (may need to check for outliers if movement sensor picked up background movement in bedroom, and user didn't bother to enter to-bed times in app).

Otherwise, decrease fatigue index.

Some other rules that may be considered are:

Decrease fatigue index on the weekend—especially if combined with long sleep duration and decreased REM.

If the user is taking a long time to fall asleep (high sleep latency), increase fatigue index (but sometimes this feature may be skewed).

If the PSQI/QOL score is bad, the user may have a sleep disorder so increase fatigue index.

If the activity data suggests the user is generally sedentary then suddenly active, increase fatigue index.

The fatigue assessment 180 could be the fatigue index value f. Alternatively, the fatigue monitoring module 110 may map the computed fatigue index value fusing one or more thresholds to one of a set of fatigue states. Such fatigue states may represent a more easily interpreted fatigue assessment 180. In one implementation of such a mapping, the set of possible fatigue states and corresponding thresholds is:

"All OK"—whereby no worrisome fatigue state is detected ($f<0.5$).

"At risk"—whereby the user has an elevated risk of fatigue ($0.5<f<0.8$). In this state, an indication of how this was derived, and the severity of same, is provided. For example, a user may be exhibiting the early stages of sleep deficit, and can correct via behavioral change before a state of chronic fatigue is experienced.

"Acute fatigue"—whereby a relatively short-term (in the order of 1-2 day) sleep restriction or very poor quality sleep is flagging likely acute fatigue ($0.8<f<1$). Based on work pattern information 135 or other data, this may be deemed to be a high-risk state (e.g., user is to perform a safety-critical function, or a user-reported planned long drive behind the wheel of a car etc.). This may initially manifest as physical fatigue, followed by increased mental fatigue (with associated cognitive impairment).

"Chronic fatigue" ($0.5<f<0.8$ for several days) can be as a result of longer term sleep restriction or general poor sleep hygiene (including poor diet, and/or a mix of caffeinated/energy drinks to stay awake, followed by alcohol and sleeping tablets to sleep)/insomnia. An underlying SDB condition can also be a root cause.

In other implementations a larger number of thresholds can be used, corresponding to a larger range of possible fatigue states.

8.1.15 User Information Module 185

The user information module 185 generates and provides a report for the user containing the fatigue state assessment and, optionally, the sleep statistics forming part of the objective sleep measures.

In a consumer implementation of the fatigue monitoring and management system 100, the user information module 185 may provide the user with personalized insights into estimated fatigue levels, risk factors, and improvement strategies.

FIG. 6 contains a schematic representation 6000 of how the user information module 185 may display objective sleep measures 120, physical activity data 115, and work pattern data 135 relative to the fatigue index f of a user over several days. In FIG. 6 the two displayed measures in the lower graph 6020 are the time asleep, and the actual work shift time. The upper graph 6010 contains the fatigue index f, in part based on these measured sleep and work shift times, calculated using the linear classifier 4000 of FIG. 4. In FIG. 6, on the second and third days 6030 and 6040, the user's fatigue index f is higher, since they have experienced short sleep periods on the preceding nights 6050 and 6060, and also longer than usual work shifts.

The user information module 185 may issue an alert if the user has not given himself or herself a sufficient opportunity for sleep (i.e., where the user has simply not allowed enough time in their routine for sleep—they may or may not be aware of this). However, in a consumer implementation of the fatigue monitoring and management system 100, an alert may not be prescriptive, as for instance travel or socializing may cause a short term or transient adverse change to fatigue state. The alert can be configured to be more prescriptive in the case of a workplace implementation, especially if the user has a safety-critical role (e.g., mining, train driver, crane operator etc.).

The fatigue assessment 180 can be used to make recommendations to the user. As an example, consider a user that has had a poor night's sleep, and that objective sleep measures 120 are collected via a non-obtrusive sleep sensor as mentioned above. During the day, fatigue-related data is captured from the user, such as objective fatigue measurements 130, environmental data 160, physical activity data 115, location data, and diet data. This data is analysed by the fatigue monitoring module 110 to generate an assessment 180 of fatigue state. The user information module 185 estimates and recommends an "ideal time to sleep" for that day based on this assessment. The user will thus know in advance what this time is and can have the option to obey or ignore the recommendation. This adherence or compliance data itself becomes an input for further analysis. Alerts may be given in advance of the recommended ideal sleep time (i.e., a 'time to sleep' reminder, e.g. delivered via the user's smartphone). Over time, the fatigue monitoring and management system develops into an individual personalised "ideal sleep time" recommender.

The user information module 185 may also, based on the predicted fatigue state under various scenarios, recommend the optimal time for the user to wake up the next day to achieve (a) optimal waking alertness, or (b) optimum all-day alertness. An alarm could be issued to the user at the recommended time via a clock app on their smartphone.

One benefit of using objective sleep measures 120 to estimate fatigue state 180 is that the user may have actually slept better than he or she perceives himself or herself to have done. Communicating this fact to the user through the user information module 185 can serve to break the vicious cycle whereby the user thinks they are going to have a bad day (psychological or delusional fatigue), followed by the excessive use of stimulants (such as coffee or other caffeinated beverages), followed by alcohol or sleeping tablets before bed. More generally, if such a pattern of stimulants is observed by the system, the user information module 185 may recommend reduction (and potentially removal) of caffeine over a time period, and similar management of alcohol intake (and smoking or "dipping" if applicable).

In the bedding application mentioned above, the user information module 185 could provide reminders to the user to change the bedding and/or environmental conditions in his or her bedroom.

In the driving implementation mentioned above, the user information module 185 could provide specific personalized recommendations for the user. This could potentially enhance safety. For example, the user information module 185 could recommend that a user seek alternative means of transport such as public transport, car-pooling (car sharing) etc. if the estimated or predicted fatigue state 180 indicates an elevated risk of falling asleep at the wheel. Over time as fatigue is monitored, estimates of geographical areas and their fatigue levels can be assessed and linked to likelihood of commuting accidents etc. The user information module 185 could also recommend a nap strategy, based on time of the day, and provide a suitable alarm to avoid over-sleep (excess napping).

In a travel implementation, the user information module 185 may recommend the user increase exposure to sun light (if possible) or utilize daylight (full spectrum) lamps/light sources during the day so as to prepare the user for an upcoming change of time zone.

In a gaming implementation, the user information module 185 may remind the user to go to bed.

In a student implementation, the user information module 185 may act as an advice engine for healthy sleep habits to enhance energy levels for study and examination times.

A benefit of CPAP therapy is reduced fatigue (e.g., reduced daytime sleepiness). An increase in fatigue index in a CPAP patient can suggest less than optimal compliance with prescribed CPAP therapy. Therefore, in a CPAP therapy implementation of the fatigue monitoring and management system 100, the user information module 185 can provide recommendations to improve the CPAP therapy compliance level of the patient. Specifically, through education (increased understanding of the linkages) delivered by the user information module 185, a patient not using their CPAP therapy regularly can be shown the benefits of increasing compliance. A high fatigue index is correlated with low therapy compliance, therefore they are motivated to improve their fatigue index, and thus their compliance.

In the case that a CPAP patient suffers from insomnia, they may choose not to use their therapy. In this scenario, by delivering personalised sleep hygiene improvement advice, and optionally offering a relaxing respiration program (guided respiration, e.g., delivered by an audio program executing on a personal computing device), the fatigue monitoring and management system 100 provides the means to enjoy better sleep, and as result increases CPAP therapy compliance.

The fatigue assessment 180 may be used to infer whether particular sequences of music used during go-to-sleep time are advantageous to promote sleep, and impact on fatigue levels the next day (e.g., identify a "fatigue busting" music track).

The fatigue assessment 180 may be used to infer whether particular breathing exercises promote sleep or alertness (e.g. alertness breathing exercises using one or more of paced illumination via a light or display device and specialised audio sequences to decrease breathing rate and modulate inspiration/expiration time, optionally with biofeedback from a non-contact sleep sensor.)

8.1.16 Third Party Information Module 190

In a workplace implementation of the fatigue monitoring and management system 100, the third party information module 190 provides a report containing information on sleep and fatigue of multiple employees to a third party such as a site health advisor of a corporate employer. The report is customizable, containing one or more of such features as:

Daily report per employee (or group of employees)

Fatigue risk metric based on factors including sleep history, time of day, and workload An indication of patterns of sleep around shifts Recent sleep history triggered on pattern of poor sleep quality or quantity Actual sleep time—duration of sleep, quality of sleep, and the timing of sleep Long term trending—including an estimate of long term sleep debt, and comparison of individual to population (i.e., comparison to the average)

Balance of restorative (deep) and cognitive (REM) sleep

Sleep disordered breathing—risk assessment

Sleep inertia (woken from deep or light sleep)

Other critical measures (therapy compliance, medication tracing etc.)

In a bedding implementation, the third party information module 190 could act as a research tool for bedding manufacturers to explore the average time of use of bedding, and relative comfort levels (entered both via subjective user data 145, and via objective sleep measures 120).

7.1.17 Sample Use Case

A sample use case of the fatigue monitoring and management system 100 for a single user is as follows. The fatigue monitoring module 110 is implemented as a software module on a cloud web server, communicating with a software application (app) on a smartphone, with wireless connectivity via Bluetooth to a non-contact sleep sensor and a wearable activity sensor for daily tracking.

Night #1: the user monitors their sleep using the non-contact sleep sensor with connectivity to the user's smartphone or other local memory storage device. This device transfers the objective sleep measures 120 such as bedtime, sleep latency (the time to fall asleep), number of interruptions, wake-up time, and a sleep score to the fatigue monitoring module 110. The snore level is also recorded overnight (via the smartphone microphone or via a microphone built in to the non-contact sleep sensor).

Day #1: In the morning, the user is presented with a Stop-Bang questionnaire as their snore level intensity and number of sleep interruptions was deemed of interest (above threshold) by the fatigue monitoring module 110. The user is also prompted to enter their height and weight, and optionally calorie consumption data. The user's physical activity data 115 is captured by a wearable activity sensor with a wireless connection to the user's smartphone for later transmission to the fatigue monitoring module 110. The user's exercise levels are compared with typical healthy values. The user is asked to log "fatigue events" via an app running on their smartphone if such are experienced during the day (e.g., yawning, eyes closing etc.). Other subjective user data 145 gathered by the smartphone includes whether the user is commuting (and if so whether they are driving), and whether the user takes naps during the day.

Night #2: The user receives their first feedback from the user information module 185 via their smartphone, including some tips on improving sleep hygiene if required. This forms the basis of user-specific calibration of fatigue.

Ongoing advice is provided by the user information module 185 during the following week.

Day #7: After a week (7 days, as it is desirable to capture a complete working week if possible), a fatigue state estimate 180 is presented either to the user by the user information module 185 or to an OH&S program administrator by the third party information module 190. Fatigue state estimates 180 may be made available before the 7-day period has elapsed, particularly if SDB patterns were detected.

The user's fatigue level is compared to population data 150, providing such parameters as the user's "real sleep age". Researchers in the field of sleep medicine have drawn up a profile of the likely distribution of sleep stages as a function of age. FIG. 5 contains a chart 5000 (from Shambroom and Fabregas) representing an example distribution of sleep stages as a function of age. By comparing a user's actual distribution of sleep stages against the population distribution, a sleep age can be determined for the user.

A quality-of-life estimate may be derived by the fatigue monitoring module 110 based on both the fatigue index, and other lifestyle parameters that may be captured by the fatigue monitoring and management system 100 as subjective user data 145. Such parameters include caffeine intake, perceived stress and energy levels, and "state of mind" (mood) estimates 7.1.18 Example Performance One example implementation of the fatigue monitoring and management system 100 made use of data collected for twenty users over seven days from the following data sources:

The Pittsburgh Sleep Questionnaire and Quality of Life survey (baseline data 155)

SleepMinder non-contact movement sensor (objective sleep measures 120 and SDB measures 125)

HOBO temperature logger (environmental data 160)

FitBit activity sensor (physical activity data 115)

PVT administered via smartphone four times daily (objective fatigue measurements 130)

VAS administered via smartphone four times daily (subjective user data 145)

Time to bed/wake up (manually entered to a smartphone app)

Ambient audio recorded by a smartphone app (environmental data 160)

A linear classifier 4000 was used to implement the fatigue monitoring module 110. The linear classifier 4000 was trained using 90% of the collected data, taking all sources except the PVT average reaction time scores as inputs. The average PVT reaction time scores for the first PVT of the day were computed as a proxy for the output fatigue index value. The trained linear classifier 4000 was then applied to test data comprising the remaining 10% of the data to predict the PVT average reaction time. FIG. 7 contains a plot of the predicted PVT average reaction time (predicted fatigue index) against the actual PVT average reaction time (actual fatigue index) on training data (circles) and test data (crosses). The RMS prediction error on the test data is 49.3 milliseconds, while on the training data it is 52.1 milliseconds, showing that the linear classifier 4000 is generalisable to unknown users. The r2 value on the test data is 0.70.

7.2 Glossary

For the purposes of the present technology disclosure, in certain forms of the present technology, one or more of the following definitions may apply. In other forms of the present technology, alternative definitions may apply.

Air: In certain forms of the present technology, air supplied to a patient may be atmospheric air, and in other forms of the present technology atmospheric air may be supplemented with oxygen.

Continuous Positive Airway Pressure (CPAP) therapy: The application of a supply of air or breathable gas to the entrance to the airways at a pressure that is continuously positive with respect to atmosphere, and preferably approximately constant through a respiratory cycle of a patient. In some forms of CPAP therapy, the pressure varies between different respiratory cycles of the patient, for example being increased in response to detection of indications of partial upper airway obstruction, and decreased in the absence of indications of partial upper airway obstruction.

Apnea: Apnea is said to have occurred when respiratory flow falls below a predetermined threshold for a duration, e.g. 10 seconds. An obstructive apnea is said to have occurred when, despite patient effort, some obstruction of the airway does not allow air to flow. A central apnea is said to have occurred when an apnea is detected that is due to a reduction in breathing effort, or the absence of breathing effort.

Breathing rate: The rate of spontaneous respiration of a patient, usually measured in breaths per minute.

Hypopnea: A hypopnea is taken to be a reduction in respiratory flow, but not a cessation of respiratory flow. In one form, a hypopnea may be said to have occurred when there is a reduction in respiratory flow below a threshold for a duration.

Patency (airway): The degree of the airway being open, or the extent to which the airway is open. A patent airway is open. Airway patency may be quantified, for example with a value of one (1) being patent, and a value of zero (0) being closed.

Respiratory flow, airflow, patient airflow, respiratory airflow (Qr): These synonymous terms may be understood to refer to the RPT device's estimate of respiratory flow rate, as opposed to "true respiratory flow" or "true respiratory airflow", which is the actual respiratory flow rate experienced by the patient, usually expressed in litres per minute.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

7.3 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

| 7.4 REFERENCE SIGNS LIST | |
|---|---|
| fatigue monitoring and management system | 100 |
| fatigue monitoring module | 110 |
| physical activity data | 115 |
| daytime vital signs | 118 |
| objective sleep measures | 120 |
| SDB measures | 125 |
| objective fatigue measurements | 130 |
| work pattern information | 135 |
| historical information | 140 |
| subjective user data | 145 |
| population data | 150 |
| baseline data | 155 |
| environmental data | 160 |
| time of day | 170 |

| 7.4 REFERENCE SIGNS LIST | |
|---|---|
| fatigue state assessment | 180 |
| user information module | 185 |
| third party information module | 190 |
| person | 1000 |
| graph | 3000 |
| first section | 3010 |
| time | 3020 |
| critical sleepy level | 3030 |
| time | 3040 |
| linear classifier | 4000 |
| chart | 5000 |
| schematic representation | 6000 |
| upper graph | 6010 |
| graph | 6020 |
| day | 6030 |
| day | 6040 |
| night | 6050 |
| night | 6060 |
| non-contact sensor | 7000 |

8 CITATIONS

Åhsberg, E., 2000. Dimensions of fatigue in different working populations. Scandinavian Journal of Psychology, 41: 231-241. http://onlinelibrary.wiley.com/doi/10.1111/1467-9450.00192/pdf Belenky, G., et al., 2003. Patterns of performance degradation and restoration during sleep restriction and subsequent recovery: a sleep dose-response study. J Sleep Res, vol. 12 no 1. http://onlinelibrary.wiley.com/doi/10.1046/j.1365-2869.2003.00337.x/pdf Dawson and Reid, 1997. Fatigue, alcohol and performance impairment. Nature, 388: 235. Dinges D F, Pack F, Williams K, Gillen K A, Powell J W, Ott G E, et al. Cumulative sleepiness, mood disturbance, and psychomotor vigilance performance decrements during a week of sleep restricted to 4-5 hours per night. Sleep 1997; 20 (4):267-77.

Harrington, J., 1978. Shiftwork and Health: A Critical Review of the Literature. Report to the Medical Advisory Service, UK Health and Safety Executive.

Institute of Medicine (US) Committee on Sleep Medicine and Research; Colten H R, Altevogt B M, editors. Sleep Disorders and Sleep Deprivation: An Unmet Public Health Problem. Washington (DC): National Academies Press (US); 2006. 4, Functional and Economic Impact of Sleep Loss and Sleep-Related Disorders. Available from: http://www.ncbi.nlm.nih.gov/books/NBK19958/63

Jackowska et al., 2012. Sleep problems and heart rate variability over the working day, Journal of Sleep Research, Volume 21, Issue 4, February 2012.

Nicholson P J, D'Auria D A, 1999. Shift work, health, the working time regulations and health assessments. Occup Med (Lond). 1999 April; 49(3): 127-37. http://occmed.oxfordjournals.org/content/49/3/127.full.pdf NSF (National Sleep Foundation), 2013. http://www.sleepfoundation.org/article/sleep-related-problems/excessive-sleepiness-and-sleep Sasaki, T., 2007. Overtime, job stressors, sleep/rest, and fatigue of Japanese workers in a company. https://www.jstage.jst.go.jp/article/indhealth/45/2/45_2_237/pdf Shahly V, Berglund P A, Coulouvrat C, et al. The Associations of Insomnia With Costly Workplace Accidents and Errors: Results From the America Insomnia Survey. Arch Gen Psychiatry. 2012: 69(10): 1054-10

Shambroom J R, Fabregas S E. Age Related Changes in Objectively Measured Sleep Observed in a Large Population in the Home, available through myzeo.com.

State of Queensland, Department of Natural Resources and Mines, 2013. Guidance Note for Fatigue Risk Management.

Trejo et al. EEG-Based Estimation of Mental Fatigue. http://aiolos.um.savba.sk/~roman/Papers/hci07_1.pdf Zichermann, G. and Cunningham, C. (August 2011). Introduction to Gamification by Design: Implementing Game Mechanics in Web and Mobile Apps (1st ed.). Sebastopol, California: O'Reilly Media.

The invention claimed is:

1. A system with one or more processors for monitoring sleep disordered breathing of a user, the system comprising:
    sensing apparatus configured to (a) generate a movement signal for the user for gathering sleep information, and to (b) generate an audio signal of breathing sounds of the user; and
    one or more processors configured to:
        (a) receive the audio signal and detect snoring events from the audio signal;
        (b) receive the movement signal to obtain sensor data representing one or more of respiratory movement and objective sleep measures; and
        (c) generate one or more sleep disordered breathing measures, wherein at least one of the one or more sleep disordered breathing measures is generated from the detected snoring events and the obtained sensor data;
    wherein the system is configured to reject snoring events that are in the audio signal and the events are not from the user by using the obtained sensor data.

2. The system of claim 1, wherein the at least one of the one or more sleep disordered breathing measures is a snoring measure, and wherein the snoring measure is determined by detecting a snoring-like event in data of the audio signal that is contemporaneous with a high frequency component in the respiratory movement.

3. The system of claim 1, wherein the system is configured to exclude detected snoring when sensor data processing indicates absence or awake.

4. The system of claim 1, wherein:
    (a) a snoring measure is restricted to intervals when data from a sensor indicates that the user is present and asleep; and/or
    (b) the system is configured to restrict snoring detection to a nearest user.

5. The system of claim 1, wherein the system is configured to exclude non-snoring sound components to exclude those sounds that are not snoring in origin.

6. The system of claim 1, wherein the system is configured to apply recognition of voice features to suppress snoring detection.

7. The system of claim 1, wherein the system is configured to correlate changes in detected snoring patterns with detection of apnea and hypopnea events from the respiratory movement.

8. The system of claim 1, wherein the system is configured to use the detected snoring events to determine whether the movement signal represents inspiration or expiration.

9. The system of claim 1, wherein:
    (a) the one or more sleep disordered breathing measures includes an elevated breathing rate;
    (b) the system is configured to correlate detected snoring events to detected sleep stages; and/or (c) the system is configured to correlate audio events related to recovery breathes from apnea with REM sleep.

10. The system of claim 1, wherein a microphone of a smartphone generates the audio signal.

11. The system of claim 1, wherein the system is configured to operate in a vicinity with more than one sleeping person, and wherein the system is configured to restrict snoring detection to the user by: (a) determining a correlation between a breathing rate determined from the audio signal and a breathing rate determined from the movement signal, or (b) determining a correlation between a detected snoring event of the audio signal and a frequency component in an inspiration phase of the movement signal.

12. The system of claim 11, wherein the system is configured to restrict snoring detection to the user by determining the correlation between a breathing rate determined from the audio signal and a breathing rate determined from the movement signal.

13. The system of claim 11, wherein the system is configured to restrict snoring detection to the user by determining the correlation between the snoring event of the audio signal and a frequency component in an inspiration phase of the movement signal.

14. A method of a system with one or more processors for monitoring sleep disordered breathing of a user, the method comprising:
with sensing apparatus:
(a) generating a movement signal for the user for gathering sleep information, and (b) generating an audio signal of breathing sounds of the user; and
in one or more processors:
(a) receiving the audio signal and detecting snoring events from the audio signal,
(b) receiving the movement signal and obtaining sensor data representing one or more of respiratory movement and objective sleep measures, and
(c) generating one or more sleep disordered breathing measures, wherein at least one of the one or more sleep disordered breathing measures is generated from the detected snoring events and the obtained sensor data;
wherein the system rejects snoring events that are in the audio signal and the events are not from the user by using the obtained sensor data.

15. The method of claim 14, wherein the at least one of the one or more sleep disordered breathing measures is a snoring measure, and wherein the snoring measure is generated by detecting a snoring-like event in data of the audio signal that is contemporaneous with a high frequency component in the respiratory movement.

16. The method of claim 14, wherein the detected snoring are excluded by the system when sensor data processing indicates absence or awake.

17. The method of claim 14, wherein:
(a) the system restricts a snoring measure to intervals when data from a sensor indicates that the user is present and asleep; and/or
(b) the system restricts snoring detection to a nearest user.

18. The method of claim 14, wherein the system excludes non-snoring sound components to exclude those sounds that are not snoring in origin.

19. The method of claim 14, wherein the system applies recognition of voice features to suppress snoring detection.

20. The method of claim 14, wherein the system correlates changes in detected snoring patterns with detection of apnea and hypopnea events from the respiratory movement.

21. The method of claim 14, wherein the system uses the detected snoring events to determine whether the movement signal represents inspiration or expiration.

22. The method of claim 14, wherein:
(a) the one or more sleep disordered breathing measures includes an elevated breathing rate;
(b) the system correlates detected snoring events to detected sleep stages; and/or
(c) the system correlates audio events related to recovery breathes from apnea with REM sleep.

23. The method of claim 14, wherein the audio signal is generated by a microphone of a smartphone.

24. The method of claim 14, wherein the system operates in a vicinity with more than one sleeping person, and wherein the system restricts snoring detection to the user by: (a) determining a correlation between a breathing rate determined from the audio signal and a breathing rate determined from the movement signal, or (b) determining a correlation between a detected snoring event of the audio signal and a frequency component in an inspiration phase of the movement signal.

25. The method of claim 24, wherein the system restricts snoring detection to the user by determining the correlation between a breathing rate determined from the audio signal and a breathing rate determined from the movement signal.

26. The method of claim 24, wherein the system restricts snoring detection to the user by determining the correlation between the snoring event of the audio signal and a frequency component in an inspiration phase of the movement signal.

27. The system of claim 1, wherein the system is configured to reject snoring events that are in the audio signal and the events are not from the user by using the obtained data by assessing a correlation of the snoring events from the audio signal with the obtained sensor data.

28. The method of claim 14, wherein the system is configured to reject snoring events that are in the audio signal and the events are not from the user by using the obtained data by assessing a correlation of the snoring events from the audio signal with the obtained sensor data.

* * * * *